(12) United States Patent
Kousaka et al.

(10) Patent No.: US 8,389,738 B2
(45) Date of Patent: Mar. 5, 2013

(54) PRODUCTION METHOD OF ISOXAZOLINE-SUBSTITUTED BENZOIC ACID AMIDE COMPOUND

(75) Inventors: Hiroyuki Kousaka, Sanyoonoda (JP);
Shunsuke Fukuya, Sanyoonoda (JP);
Yuji Moriyama, Funabashi (JP);
Manabu Yaosaka, Funabashi (JP);
Takashi Mizukoshi, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 207 days.

(21) Appl. No.: 13/002,837

(22) PCT Filed: Jul. 9, 2009

(86) PCT No.: PCT/JP2009/062516
§ 371 (c)(1),
(2), (4) Date: Feb. 15, 2011

(87) PCT Pub. No.: WO2010/005048
PCT Pub. Date: Jan. 14, 2010

(65) Prior Publication Data
US 2011/0144349 A1 Jun. 16, 2011

(30) Foreign Application Priority Data

Jul. 9, 2008 (JP) ................................. 2008-178621
Jun. 24, 2009 (JP) ................................. 2009-149401

(51) Int. Cl.
*C07D 261/04* (2006.01)
(52) U.S. Cl. ........................................................ 548/240
(58) Field of Classification Search .................... None
See application file for complete search history.

(56) References Cited

U.S. PATENT DOCUMENTS

| 2007/0066617 A1 | 3/2007 | Mita et al. |
| 2010/0144797 A1 | 6/2010 | Mita et al. |

FOREIGN PATENT DOCUMENTS

| JP | A-2002-88024 | 3/2002 |
| WO | WO 2005/085216 A1 | 9/2005 |
| WO | WO 2007/041130 A2 | 4/2007 |
| WO | WO 2007/079162 A1 | 7/2007 |
| WO | WO 2008/108448 A1 | 9/2008 |

OTHER PUBLICATIONS

May 25, 2012 Search Report issued in European Patent Application No. EP 09 79 4492.
Falgueyret et al., "Lysosomotropism of Basic Cathepsin K Inhibitors Contributes to Increased Cellular Potencies against Off-Target Cathepsins and Reduced Functional Selecivity," *J. Med. Chem.*, 2005, pp. 7535-7543, vol. 48, American Chemical Society.
International Search Report for International Patent Application No. PCT/JP2009/062516, mailed on Sep. 1, 2009.

*Primary Examiner* — Kamal Saeed
(74) *Attorney, Agent, or Firm* — Oliff & Berridge, PLC

(57) ABSTRACT

A production method of an isoxazoline-substituted benzoic acid amide compound of Formula (1) where X is a halogen atom, $C_{1-6}$ haloalkyl, etc., Y is a halogen atom, $C_{1-6}$ alkyl, etc., $R^1$ is a $C_{1-6}$ haloalkyl, etc., $R^2$ and $R^3$ independently of each other are a hydrogen atom, $C_{1-6}$ alkyl, etc., $R^4$ is $C_{1-6}$ alkyl, $C_{1-6}$ haloalkyl, etc., $R^5$ is a hydrogen atom, $c_{1-6}$ alkyl, etc., m is an integer of 0 to 5, n is an integer of 0 to 4, including: reacting an isoxazoline-substituted benzene compound of Formula (3) where X, Y, $R^1$, m, and n are the same as defined above, L is a chlorine atom, a bromine atom, —C(O)OH, —C(O)J, etc., J is a halogen atom, with a 2-aminoacetic acid amide compound of Formula (2) where $R^2$, $R^3$, $R^4$, and $R^5$ are the same as defined above, or a salt thereof; crystal forms and the production method thereof.

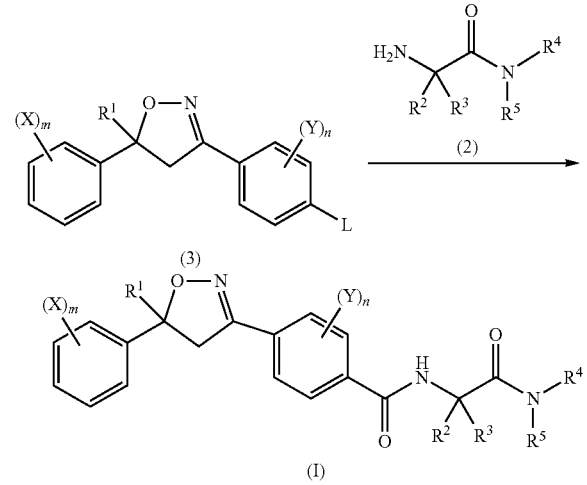

8 Claims, 2 Drawing Sheets

PRODUCTION METHOD OF ISOXAZOLINE-SUBSTITUTED BENZOIC ACID AMIDE COMPOUND

TECHNICAL FIELD

The present invention relates to a production method of an isoxazoline-substituted benzoic acid amide compound useful as a pest control agent and disclosed in, for example, WO 05/085216 pamphlet and WO 2009/024541 pamphlet.

BACKGROUND ART

A production method via N-(isoxazoline-substituted benzoyl)glycine (for example, see Patent Document 1) is known as a production method of an isoxazoline-substituted benzoic acid amide compound of Formula (1) in the present invention.

RELATED-ART DOCUMENT

Patent Document

Patent Document 1: WO 05/085216 pamphlet

DISCLOSURE OF THE INVENTION

Problem to be Solved by the Invention

It is an object of the present invention to provide an industrial production method of an isoxazoline-substituted benzoic acid amide compound useful as a pest control agent.

Means for Solving the Problem

As a result of assiduous research on the production method of an isoxazoline-substituted benzoic acid amide compound, the inventors of the present invention have completed the present invention, and an object of the present invention is to provide a production method of an isoxazoline-substituted benzoic acid amide compound of Formula (1) useful as a pest control agent.

The present invention relates to [1] to [4].

[1] A production method of an isoxazoline-substituted benzoic acid amide compound of Formula (1):

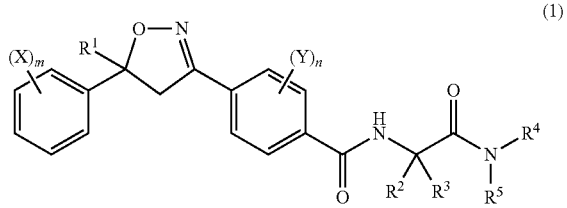

[where X is a halogen atom, cyano, nitro, —$SF_5$, $C_{1-6}$ alkyl, $C_{1-4}$ haloalkyl, hydroxy($C_{1-6}$)alkyl, hydroxy($C_{1-6}$)haloalkyl, $C_{1-6}$ alkoxy($C_{1-6}$)alkyl, $C_{1-6}$ haloalkoxy ($C_{1-6}$)alkyl, $C_{1-6}$ alkoxy($C_{1-6}$)haloalkyl, $C_{1-6}$ haloalkoxy($C_{1-6}$)halo alkyl, $C_{3-8}$ cycloalkyl, $C_{3-8}$ halocycloalkyl, —$OR^6$, —$OSO_2R^6$, —$S(O)_r R^6$, or —$N(R^8)R^7$, where when m is 2 or more, Xs are optionally the same as or different from each other, Y is a halogen atom, cyano, nitro, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{1-6}$ alkylsulfonyl, $C_{1-6}$ haloalkylsulfonyl, or —$N(R^8)R^7$, where when n is 2 or more, Ys are optionally the same as or different from each other, $R^1$ is a hydrogen atom, $C_{1-6}$ alkyl, $C_{1-6}$ haloalkyl, $C_{3-8}$ cycloalkyl, or $C_{3-8}$ halocycloalkyl, $R^2$ is a hydrogen atom, cyano, $C_{1-6}$ alkyl, or $C_{1-6}$ haloalkyl, $R^3$ is a hydrogen atom or $C_{1-6}$ alkyl, or $R^3$ together with $R^2$ optionally form a $C_{2-5}$ alkylene chain to form together with a carbon atom to which $R^3$ is bonded a 3- to 6-membered ring, and at this time, the alkylene chain optionally contains one oxygen atom, one sulfur atom, or one nitrogen atom, $R^4$ is a hydrogen atom, $C_{1-6}$ alkyl, $C_{1-6}$ alkyl optionally substituted with $R^{11}$, $C_{1-6}$ haloalkyl, $C_{3-8}$ cycloalkyl, $C_{3-8}$ halocycloalkyl, $C_{3-6}$ alkenyl, $C_{3-6}$ haloalkenyl, $C_{3-6}$ alkynyl, phenyl, or phenyl substituted with $(Z)_t$, $R^5$ is a hydrogen atom, $C_{1-6}$ alkyl, $C_{1-6}$ haloalkyl, $C_{3-8}$ cycloalkyl, $C_{3-8}$ halocycloalkyl, —CHO, $C_{1-6}$ alkylcarbonyl, $C_{1-6}$ haloalkylcarbonyl, $C_{1-6}$ alkoxycarbonyl, $C_{1-6}$ alkylsulfonyl, or $C_{1-6}$ haloalkylsulfonyl, or $R^5$ together with $R^4$ optionally form a $C_{2-6}$ alkylene chain to form together with a nitrogen atom to which $R^5$ is bonded a 3- to 7-membered ring, and at this time, the alkylene chain optionally contains one oxygen atom, one sulfur atom, or one nitrogen atom and is optionally substituted with a halogen atom, a $C_{1-6}$ alkyl group, a $C_{1-6}$ alkoxy group, a formyl group, a $C_{1-6}$ alkylcarbonyl group, a $C_{1-6}$ alkoxycarbonyl group, an oxo group, or a thioxo group, $R^6$ is $C_{1-6}$ alkyl, $C_{1-4}$ alkoxy($C_{1-4}$)alkyl, $C_{1-6}$ haloalkyl, or $C_{1-4}$ haloalkoxy($C_{1-4}$)haloalkyl, $R^7$ is $C_{1-6}$ alkyl, —CHO, $C_{1-6}$ alkylcarbonyl, $C_{1-6}$ haloalkylcarbonyl, $C_{1-6}$ alkoxycarbonyl, $C_{1-6}$ alkylsulfonyl, or $C_{1-6}$ haloalkylsulfonyl, $R^8$ is a hydrogen atom or $C_{1-6}$ alkyl, $R^{11}$ is cyano, $C_{3-8}$ cycloalkyl, $C_{3-8}$ halocycloalkyl, —$OR^6$, —$S(O)_r R^6$, —$N(R^8)R^7$, phenyl, or phenyl substituted with $(Z)_t$, Z is a halogen atom, cyano, nitro, $C_{1-6}$ alkyl, $C_{1-6}$ haloalkyl, $C_{3-8}$ cycloalkyl, $C_{3-8}$ halocycloalkyl, —$OR^6$, —$OSO_2R^6$, —$S(O)_r R^6$, or —$N(R^8)R^7$, where when t is 2 or more, Zs are optionally the same as or different from each other, m is an integer of 0 to 5, n is an integer of 0 to 4, r is an integer of 0 to 2, and t is an integer of 1 to 5], the production method comprising: reacting an isoxazoline-substituted benzene compound of Formula (3);

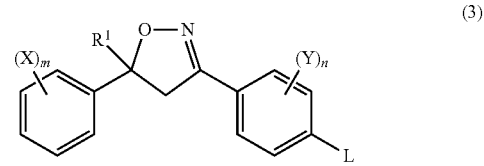

[where X, Y, $R^1$, m, and n are the same as defined above,

L is a chlorine atom, a bromine atom, an iodine atom, —$OSO_2R^9$, —C(O)OH, —C(O)$OR^{10}$, or —C(O)J, $R^9$ is $C_{1-6}$ alkyl, $C_{1-6}$ haloalkyl, phenyl, or phenyl substituted with $(Z)_t$, $R^{10}$ is $C_{1-6}$ alkyl, $C_{1-4}$ alkoxy($C_{1-4}$)alkyl, $C_{1-6}$ haloalkyl, $C_{1-4}$ haloalkoxy($C_{1-4}$)haloalkyl, benzyl, phenyl, or phenyl substituted with $(Z)_t$, Z, r and t are the same as defined above, and
J is a halogen atom],
with a 2-aminoacetic acid amide compound of Formula (2):

$$
H_2N \underset{R^2\ R^3}{\overset{O}{\underset{\|}{C}}} \underset{R^5}{N} R^4 \tag{2}
$$

[where $R^2$, $R^3$, $R^4$, and $R^5$ are the same as defined above] or a salt thereof.

[2] The production method of an isoxazoline-substituted benzoic acid amide compound according to [1], characterized in that a compound of Formula (3) (where L is a chlorine atom, a bromine atom, an iodine atom, or —$OSO_2R^9$) is reacted with a compound of Formula (2) in the presence of carbon monoxide and a palladium catalyst.

[3] The production method of an isoxazoline-substituted benzoic acid amide compound according to [1], characterized in that a compound of Formula (3) (where L is —C(O)OH) is reacted with a compound of Formula (2) in the presence of a condensing agent.

[4] The production method of an isoxazoline-substituted benzoic acid amide compound according to [1], characterized in that a compound of Formula (3) (where L is —$C(O)OR^{10}$ or —C(O)J) is reacted with a compound of Formula (2) in the presence of a base,

[5] The production method of a compound of Formula (1-1):

$$(1\text{-}1)$$

according to [1] to [4].

[6] A I-form crystal of a compound of Formula (1-1) in which a diffraction angle (2θ) in a powder X-ray diffraction spectrum has peaks at 4.4°, 8.7°, 11.1°, 13.1°, 14.4°, 14.8°, 16.3°, 16.9°, 17.4°, 17.7°, 18.1°, 18.8°, 19.4°, 21.2°, 21.9°, 22.3°, 23.0°, 23.9°, 24.5°, 25.0°, 26.3°, and 27.3°.

[7] The I-form crystal according to [6] having substantially the same pattern as that of the powder X-ray diffraction spectrum exemplified in FIG. 1.

[8] A II-form crystal of a compound of Formula (1-1) in which a diffraction angle (2θ) in a powder X-ray diffraction spectrum has peaks at 10.2°, 12.3°, 14.7°, 15.9°, 18.4°, 20.1°, 21.2°, 22.0°, 22.8°, 24.6°, and 26.6°.

[9] The II-form crystal according to [8] having substantially the same pattern as that of the powder X-ray diffraction spectrum exemplified in FIG. 2.

[10] A III-form crystal of a compound of Formula (1-1) in which a diffraction angle (2θ) in a powder X-ray diffraction spectrum has peaks at 4.3°, 8.7°, 11.1°, 14.4°, 16.3°, 16.9°, 17.4°, 7.7°, 18.7°, 19.4°, 19.9°, 21.2°, 21.8°, 22.3°, 23.8°, 24.4°, 24.9°, and 26.2°.

[11] The III-form crystal according to [10] having substantially the same pattern as that of the powder X-ray diffraction spectrum exemplified in HG 3.

[12] An amorphous substance of a compound of Formula (1-1).

[13] The amorphous substance according to [12] having substantially the same pattern as that of the powder X-ray diffraction spectrum exemplified in FIG. 4, that is, having no diffraction peak.

[14] A production method of the II-form crystal described in [8] or [9], characterized by including precipitating the II-form crystal from a hydrous organic solution of a compound of Formula (1-1) under a stationary condition.

[15] A production method of the II-form crystal described in [8] or [9], characterized by including transferring other crystal forms in methanol.

[16] A production method of the III-form crystal described in [10] or [11], characterized by including rapidly precipitating the crystal from a solution containing a compound of Formula (1-1).

[17] A production method of the amorphous substance described in [12] or [13], characterized by including dropping a solution in which a compound of Formula (1-1) is dissolved in acetic acid or dimethylsulfoxide into water.

[18] A production method of the I-form crystal described in [6] or [7], characterized by including transferring the III-form crystal described in [10] or [11].

[19] A production method of the I-form crystal described in [6] or [7], characterized by including transferring the III-form crystal described in [10] or [11] in a suspension.

[20] A production method of the I-form crystal described in [6] or [7], characterized by including transferring the III-form crystal described in [10] or [11] in a toluene suspension.

[21] A production method of the I-form crystal described in [6] or [7], characterized by including crystallizing the amorphous substance described in [12] or [13].

[22] A production method of the I-form crystal described in [6] or [7], characterized by including crystallizing the amorphous substance described in [12] or [13] in a suspension.

[23] A production method of the I-form crystal described in [6] or [7], characterized by including crystallizing the amorphous substance described in [12] or [13] in a toluene suspension.

Effects of the Invention

The present invention can provide an industrial production method of a compound having excellent insecticidal and miticidal activity against agricultural insect pests, spider mites, and internal or external parasites of mammals or birds disclosed in, for example, WO 05/085216 pamphlet.

BEST MODES FOR CARRYING OUT THE INVENTION

Figure 1:
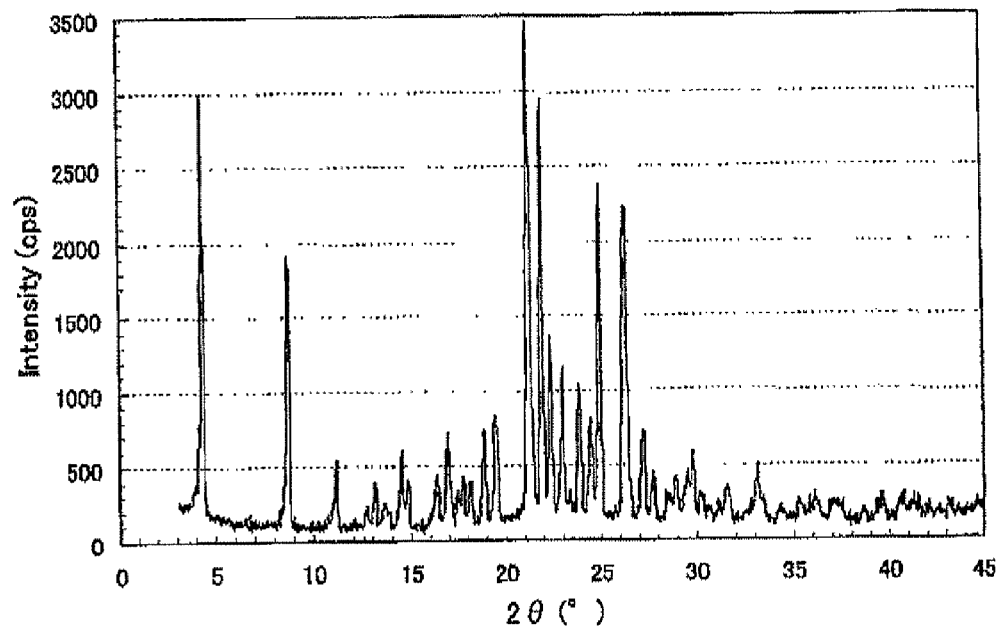
FIG. 1 shows a powder X-ray diffraction pattern of a I-form crystal of a compound of Formula (1-1).

The compounds of Formula (1), (2), and (3) of the present invention have optically active substances due to the presence of one asymmetric carbon atom. However, the present invention includes all of optically active substances, racemic bodies; and mixtures of the optically active substances in any mixing ratio.

Examples of the compounds encompassed in the present invention capable of being converted into an acid addition salt by a common method include: salts of halogenated hydrogen acids such as hydrofluoric acid, hydrochloric acid, hydrobromic acid, and hydroiodic acid; salts of inorganic acids such as nitric acid, sulfuric acid, phosphoric acid, chloric acid, and perchloric acid; salts of sulfonic acids such as methanesulfonic acid, ethanesulfonic acid, trifluoromethanesulfonic acid, benzenesulfonic acid, and p-toluenesulfonic acid; salts of carboxylic acids such as formic acid, acetic acid, propionic acid, trifluoroacetic acid, fumaric acid, tartaric acid, oxalic acid, maleic acid, malic acid, succinic acid, benzoic acid, mandelic acid, ascorbic acid, lactic acid, gluconic acid, and citric acid; and salts of amino acids such as glutamic acid and aspartic acid.

Examples of the compounds encompassed in the present invention capable of being converted into a metal salt by a common method include: salts of alkali metals such as lithium, sodium, and potassium; salts of alkaline earth metals such as calcium, barium, and magnesium; and salts of aluminum.

Moreover, examples of the compounds encompassed in the present invention capable of being converted into an amine salt by a common method include salts of trimethylamine, triethylamine, tributylamine, diisopropylethylamine, N,N,N', N'-tetramethylethylenediamine, N,N-dimethylaniline, pyridine, 5-ethyl-2-methylpyridine, 4-(dimethylamino)pyridine, and 1,8-diazabicyclo[5,4,0]-7-undecene.

Next, specific examples of each substituent shown in the present specification are shown below. Here, n-, i-, s-, and t- mean normal-, iso-, secondary-, and tertiary-, respectively.

Examples of the halogen atom in the compound of the present invention include a fluorine atom, a chlorine atom, a bromine atom, and an iodine atom. Here, the expression "halo" in the present specification is these halogen atoms.

The expression "$C_{a-b}$ alkyl" in the present specification is straight-chain or branched-chain hydrocarbon groups having carbon atom number of a to b, and specific examples thereof include a methyl group, an ethyl group, an n-propyl group, an i-propyl group, an n-butyl group, an i-butyl group, an s-butyl group, a t-butyl group, an n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a 2,2-dimethylpropyl group, an n-hexyl group, a 1-methylpentyl group, a 2-methylpentyl group, a 1,1-dimethylbutyl group, and a 1,3-dimethylbutyl group. Each alkyl group of "$C_{a-b}$ alkyl" is selected from within the range of a specified number of carbon atoms.

The expression "$C_{a-b}$ haloalkyl" in the present specification is straight-chain or branched-chain hydrocarbon groups having carbon atom number of a to b in which hydrogen atoms bonded to a carbon atom are arbitrarily substituted with halogen atoms. At this time, when two or more hydrogen atoms are substituted with two or more halogen atoms, these halogen atoms may be the same as or different from each other. Specific examples of the "$C_{a-b}$ haloalkyl" include a fluoromethyl group, a chloromethyl group, a bromomethyl group, an iodomethyl group, a difluoromethyl group, a chlorofluoromethyl group, a dichloromethyl group, a bromofluoromethyl group, a trifluoromethyl group, a chlorodifluoromethyl group, a dichlorofluoromethyl group, a trichloromethyl group, a bromodifluoromethyl group, a bromochlorofluoromethyl group, a dibromofluoromethyl group, a 2-fluoroethyl group, a 2-chloroethyl group, a 2-bromoethyl group, a 2,2-difluoroethyl group, a 2-chloro-2-fluoroethyl group, a 2,2-dichloroethyl group, a 2-bromo-2-fluoroethyl group, a 2,2,2-trifluoroethyl group, a 2-chloro-2,2-difluoroethyl group, a 2,2-dichloro-2-fluoroethyl group, a 2,2,2-trichloroethyl group, a 2-bromo-2,2-difluoroethyl group, a 2-bromo-2-chloro-2-fluoroethyl group, a 2-bromo-2,2-dichloroethyl group, a 1,1,2,2-tetrafluoroethyl group, a pentafluoroethyl group, a 1-chloro-1,2,2,2-tetrafluoroethyl group, a 2-chloro-1,1,2,2-tetrafluoroethyl group, a 1,2-dichloro-1,2,2-trifluoroethyl group, a 2-bromo-1,1,2,2-tetrafluoroethyl group, a 2-fluoropropyl group, a 2-chloropropyl group, a 2-bromopropyl group, a 2-chloro-2-fluoropropyl group, a 2,3-dichloropropyl group, a 2-bromo-3-fluoropropyl group, a 3-bromo-2-chloropropyl group, a 2,3-dibromopropyl group, a 3,3,3-trifluoropropyl group, a 3-bromo-3,3-difluoropropyl group, a 2,2,3,3-tetrafluoropropyl group, a 2-chloro-3,3,3-trifluoropropyl group, a 2,2,3,3,3-pentafluoropropyl group, a 1,1,2,3,3,3-hexafluoropropyl group, a heptafluoropropyl group, a 2,3-dichloro-1,1,2,3,3-pentafluoropropyl group, a 2-fluoro-1-methylethyl group, a 2-chloro-1-methylethyl group, a 2-bromo-1-methylethyl group, a 2,2,2-trifluoro-1-(trifluoromethyl)ethyl group, a 1,2,2,2-tetrafluoro-1-(trifluoromethyl)ethyl group, a 2-fluorobutyl group, a 2-chlorobutyl group, a 2,2,3,3,4,4-hexafluorobutyl group, a 2,2,3,4,4,4-hexafluorobutyl group, a 2,2,3,3,4,4,4-hexafluorobutyl group, a 2,2,3,3,4,4,4-heptafluorobutyl group, a 1,1,2,2,3,3,4,4-octafluorobutyl group, a nonafluorobutyl group, a 4-chloro-1,1,2,2,3,3,4,4-octafluorobutyl group, a 2-fluoro-2-methylpropyl group, a 1,2,2,3,3,3-hexafluoro-1-(trifluoromethyl)propyl group, a 2-chloro-1,1-dimethylethyl group, a 2-bromo-1,1-dimethylethyl group, and a 5-chloro-2,2,3,4,4,5,5-heptafluoropentyl group. Each haloalkyl group of "$C_{a-b}$ haloalkyl" is selected from within the range of a specified number of carbon atoms.

The expression "$C_{a-b}$ cycloalkyl" in the present specification is cyclic hydrocarbon groups having carbon atom number of a to b capable of forming a monocyclic or composite ring structure containing a 3-membered ring to a 6-membered ring. Each ring may arbitrarily be substituted with an alkyl group within the range of a specified number of carbon atoms. Specific examples of the "$C_{a-b}$ cycloalkyl" include a cyclopropyl group, a 1-methylcyclopropyl group, a 2-methylcyclopropyl group, a 2,2-dimethylcyclopropyl group, a 2,2,3,3-tetramethylcyclopropyl group, a cyclobutyl group, a cyclopentyl group, a 2-methylcyclopentyl group, a 3-methylcyclopentyl group, a cyclohexyl group, a 2-methylcyclohexyl group, a 3-methylcyclohexyl group, a 4-methylcyclohexyl group, and a bicyclo[2.2.1]heptane-2-yl group. Each cycloalkyl group of "$C_{a-b}$ cycloalkyl" is selected from within the range of a specified number of carbon atoms.

The expression "$C_{a-b}$ halocycloalkyl" in the present specification is cyclic hydrocarbon groups having carbon atom number of a to b in which hydrogen atoms bonded to a carbon atom are arbitrarily substituted with halogen atoms and which is capable of forming a monocyclic or composite ring structure containing a 3-membered ring to a 6-membered ring. Each ring may arbitrarily be substituted with an alkyl group within the range of a specified number of carbon atoms, and the substitution of hydrogen atoms with halogen atoms may, be performed in any one of a ring structure part, a side chain part, and both of them. Furthermore, when two or more hydrogen atoms are substituted with two or more halogen atoms, these halogen atoms may be the same as or different from each other. Specific examples of the "$C_{a-b}$ halocycloalkyl" include a 2,2-difluorocyclopropyl group, a 2,2-dichlorocyclopropyl group, a 2,2-dibromocyclopropyl group, a 2,2-difluoro-1-methylcyclopropyl group, a 2,2- dichloro-1-methylcyclopropyl group, a 2,2-dibromo-1-methylcyclopropyl group, a 2,2,3,3-tetrafluorocyclobutyl group, a 2-(trifluoromethyl)cyclohexyl group, a 3-(trifluoromethyl)cyclohexyl group, and a 4-(trifluoromethyl)cyclohexyl group. Each halocycloalkyl group of "$C_{a-b}$ halocycloalkyl" is selected from within the range of a specified number of carbon atoms.

The expression "$C_{a-b}$ alkenyl" in the present specification is straight-chain or branched-chain unsaturated hydrocarbon groups having carbon atom number of a to b and having one or two or more double bond(s) in the molecule thereof, and specific examples thereof include a vinyl group, a 1-propenyl group, a 2-propenyl group, a 1-methylethenyl group, a 2-butenyl group, a 1-methyl-2-propenyl group, a 2-methyl-2-propenyl group, a 2-pentenyl group, a 2-methyl-2-butenyl group, a 3-methyl-2-butenyl group, a 2-ethyl-2-propenyl group, a 1,1-dimethyl-2-propenyl group, a 2-hexenyl group, a 2-methyl-2-pentenyl group, a 2,4-dimethyl-2,6-heptadienyl group, and a 3,7-dimethyl-2,6-octadienyl group. Each alkenyl group of "$C_{a-b}$ alkenyl" is selected from within the range of a specified number of carbon atoms.

The expression "$C_{a-b}$ haloalkenyl" in the present specification is straight-chain or branched-chain unsaturated hydrocarbon groups having carbon atom number of a to b and having one or two or more double bond(s) in the molecule thereof in which a hydrogen atom bonded to a carbon atom is arbitrarily substituted with a halogen atom. At this time, when two or more hydrogen atoms are substituted with two or more halogen atoms, these halogen atoms may be the same as or different from each other. Specific examples of the "$C_{a-b}$ haloalkenyl" include a 2,2-dichlorovinyl group, a 2-fluoro-2-propenyl group, a 2-chloro-2-propenyl group, a 3-chloro-2-propenyl group, a 2-bromo-2-propenyl group, a 3-bromo-2-propenyl group, a 3,3-difluoro-2-propenyl group, a 2,3-dichloro-2-propenyl group, a 3,3-dichloro-2-propenyl group, a 2,3-dibromo-2-propenyl group, a 2,3,3-trifluoro-2-propenyl group, a 2,3,3-trichloro-2-propenyl group, a 1-(trifluoromethyl)ethenyl group, a 3-chloro-2-butenyl group, a 3-bromo-2-butenyl group, a 4,4-difluoro-3-butenyl group, a 3,4,4-trifluoro-3-butenyl group, a 3-chloro-4,4,4-trifluoro-2-butenyl group, and 3-bromo-2-methyl-2-propenyl group. Each haloalkenyl group of "$C_{a-b}$ haloalkenyl" is selected from within the range of a specified number of carbon atoms.

The expression "$C_{a-b}$ alkynyl" in the present specification is straight-chain or branched-chain unsaturated hydrocarbon groups having carbon atom number of a to b and having one or two or more triple bond(s) in the molecule thereof, and specific examples thereof include an ethynyl group, a 1-propynyl group, a 2-propynyl group, a 2-butynyl group, a 1-methyl-2-propynyl group, a 2-pentynyl group, a 1-methyl-2-butynyl group, a 1,1-dimethyl-2-propynyl group, and a 2-hexynyl group. Each alkynyl group of "$C_{a-b}$ alkynyl" is selected from within the range of a specified number of carbon atoms.

The expression "$C_{a-b}$ alkoxy" in the present specification is alkyl-O— groups having carbon atom number of a to b in which the alkyl is as defined above, and specific examples thereof include a methoxy group, an ethoxy group, an n-propyloxy group, an i-propyloxy group, an n-butyloxy group, an i-butyloxy group, an s-butyloxy group, a t-butyloxy group, an n-pentyloxy group, and an n-hexyloxy group. Each alkoxy group of "$C_{a-b}$ alkoxy" is selected from within the range of a specified number of carbon atoms.

The expression "$C_{a-b}$ haloalkoxy" in the present specification is haloalkyl-O— groups having carbon atom number of a to b in which the haloalkyl is as defined above, and specific examples thereof include a difluoromethoxy group, a trifluoromethoxy group, a chlorodifluoromethoxy group, a bromodifluoromethoxy group, a 2-fluoroethoxy group, a 2-chloroethoxy group, a 2,2,2-trifluoroethoxy group, a 1,1,2,2-tetrafluoroethoxy group, a 2-chloro-1,1,2-trifluoroethoxy group, a 2-bromo-1,1,2-trifluoroethoxy group, a pentafluoroethoxy group, a 2,2-dichloro-1,1,2-trifluoroethoxy group, a 2,2,2-trichloro-1,1-difluoroethoxy group, a 2-bromo-1,1,2,2-tetrafluoroethoxy group, a 2,2,3,3-tetrafluoropropyloxy group, a 1,1,2,3,3,3-hexafluoropropyloxy group, a 2,2,2-trifluoro-1-(trifluoromethyl)ethoxy group, a heptafluoropropyloxy group, and a 2-bromo-1,1,2,3,3,3-hexafluoropropyloxy group. Each haloalkoxy group of "$C_{a-b}$ haloalkoxy" is selected from within the range of a specified number of carbon atoms.

The expression "$C_{a-b}$ alkylthio" in the present specification is alkyl-S— groups having carbon atom number of a to b in which the alkyl is as defined above, and specific examples thereof include a methylthio group, an ethylthio group, an n-propylthio group, an i-propylthio group, an n-butylthio group, an i-butylthio group, an s-butylthio group, and a t-butylthio group. Each alkylthio group of "$C_{a-b}$ alkylthio" is selected from within the range of a specified number of carbon atoms.

The expression "$C_{a-b}$ haloalkylthio" in the present specification is haloalkyl-S— groups having carbon atom number of a to b in which the haloalkyl is as defined above, and specific examples thereof include a difluoromethylthio group, a trifluoromethylthio group, a chlorodifluoromethylthio group, a bromodifluoromethylthio group, a 2,2,2-trifluoroethylthio group, a 1,1,2,2-tetrafluoroethylthio group, a 2-chloro-1,1,2-trifluoroethylthio group, a pentafluoroethylthio group, a 2-bromo-1,1,2,2-tetrafluoroethylthio group, a 1,1,2,3,3,3-hexafluoropropylthio group, a heptafluoropropylthio group, a 1,2,2,2-tetrafluoro-1-(trifluoromethyl)ethylthio group, and a nonafluorobutylthio group. Each haloalkylthio group of "$C_{a-b}$ haloalkylthio" is selected from within the range of a specified number of carbon atoms.

The expression "$C_{a-b}$ alkylsulfonyl" in the present specification is alkyl-$SO_2$— groups having carbon atom number of a to b in which the alkyl is as defined above, and specific examples thereof include a methylsulfonyl group, an ethylsulfonyl group, an n-propylsulfonyl group, an i-propylsulfonyl group, an n-butylsulfonyl group, an i-butylsulfonyl group, an s-butylsulfonyl group, and a t-butylsulfonyl group. Each alkylsulfonyl group of "$C_{a-b}$ alkylsulfonyl" is selected from within the range of a specified number of carbon atoms.

The expression "$C_{a-b}$ haloalkylsulfonyl" in the present specification is haloalkyl-$SO_2$— groups having carbon atom number of a to b in which the haloalkyl is as defined above, and specific examples thereof include a difluoromethylsulfonyl group, a trifluoromethylsulfonyl group, a chlorodifluoromethylsulfonyl group, a bromodifluoromethylsulfonyl group, a 2,2,2-trifluoroethylsulfonyl group, a 1,1,2,2-tetrafluoroethylsulfonyl group, a 2-chloro-1,1,2-trifluoroethylsulfonyl group, and a 2-bromo-1,1,2,2-tetrafluoroethylsulfonyl group. Each haloalkylsulfonyl group of "$C_{a-b}$ haloalkylsulfonyl" is selected from within the range of a specified number of carbon atoms.

The expression "$C_{a-b}$ alkylcarbonyl" in the present specification is alkyl-C(O)— groups having carbon atom number of a to b in which the alkyl is as defined above, and specific examples thereof include an acetyl group, a propionyl group, a butyryl group, an isobutyryl group, a valeryl group, an isovaleryl group, a 2-methylbutanoyl group, pivaloyl group, and a hexanoyl group. Each alkylcarbonyl group of "$C_{a-b}$ alkylcarbonyl" is selected from within the range of a specified number of carbon atoms.

The expression "$C_{a-b}$ haloalkylcarbonyl" in the present specification is haloalkyl-C(O)— groups having carbon atom number of a to b in which the haloalkyl is as defined above, and specific examples thereof include a fluoroacetyl group, a chloroacetyl group, a difluoroacetyl group, a dichloroacetyl group, a trifluoroacetyl group, a chlorodifluoroacetyl group, a bromodifluoroacetyl group, a trichloroacetyl group, a pentafluoropropionyl group, a heptafluorobutanoyl group, and a 3-chloro-2,2-dimethylpropanoyl group. Each haloalkylcarbonyl group of "$C_{a-b}$ haloalkylcarbonyl" is selected from within the range of a specified number of carbon atoms.

The expression "$C_{a-b}$ alkoxycarbonyl" in the present specification is alkyl-O—C(O)— groups having carbon atom number of a to b in which the alkyl is as defined above, and specific examples thereof include a methoxycarbonyl group, an ethoxycarbonyl group, an n-propyloxycarbonyl group, an i-propyloxycarbonyl group, an n-butoxycarbonyl group, an i-butoxycarbonyl group, and a t-butoxycarbonyl group. Each alkoxycarbonyl group of "$C_{a-b}$ alkoxycarbonyl" is selected from within the range of a specified number of carbon atoms.

The expression "hydroxy($C_{d-e}$)alkyl", "$C_{a-b}$ alkoxy($C_{d-e}$) alkyl", or "$C_{a-b}$ haloalkoxy($C_{de}$) alkyl" in the present specification is individually straight-chain or branched-chain hydrocarbon groups having carbon atom number of d to e in which hydrogen atoms bonded to a carbon atom are arbitrarily substituted with any one of a $C_{a-b}$ alkoxy group as defined above; a $C_{a-b}$ haloalkoxy group as defined above, and a hydroxy group. Specific examples thereof include a hydroxymethyl group, a 1-hydroxyethyl group, a 2-hydroxyethyl group, a 2-hydroxypropyl group, a 3-hydroxypropyl group, a 2-hydroxybutyl group, a methoxymethyl group, an ethoxymethyl group, a methoxy-2-ethyl group, a 2-chloroethoxymethyl group, and a 2,2,2-trifluoroethoxymethyl group. Each of these groups is selected from within the range of a specified number of carbon atoms.

The expression "hydroxy($C_{d-e}$) haloalkyl", "$C_{a-b}$ alkoxy ($C_{d-e}$) haloalkyl", or "$C_{a-b}$ haloalkoxy($C_{d-e}$) haloalkyl" in the present specification is individually haloalkyl groups as defined above having carbon atom number of d to e in which hydrogen atoms or halogen atoms bonded to a carbon atom are arbitrarily substituted with any one of a $C_{a-b}$ alkoxy group as defined above, a $C_{a-b}$ haloalkoxy group as defined above, or a hydroxy group. Specific examples thereof include a 2,2,2-trifluoro-1-hydroxy-1-(trifluoromethyl)ethyl group, a difluoro(methoxy)methyl group, a 2,2,2-trifluoro-1-methoxy-1-(trifluoromethyl)ethyl group, a difluoro(2,2,2-trifluoroethoxy)methyl group, a 2,2,2-trifluoro-1-(2,2,2-trifluoroethoxy)-1-(trifluoromethyl)ethyl group, and a 3-(1,2-dichloro-1,2,2-trifluoroethoxy)-1,1,2,2,3,3-hexafluoropropyl group. Each of these groups is selected from within the range of a specified number of carbon atoms.

In the compound encompassed in the present invention, preferred examples of the substituent of X include a halogen atom, $C_{1-4}$ alkyl, and $C_{1-4}$ haloalkyl, more preferred examples thereof include a chlorine atom, a bromine atom, an, iodine atom, methyl, and trifluoromethyl, and most preferred examples thereof include a chlorine atom, a bromine atom, and trifluoromethyl. At this time, when m that is the number of substituents of X is an integer of 2 or more Xs may be the same as or different from each other.

In the compound encompassed in the present invention, preferred examples of m that is the number of substituents of X include 1 to 3.

In the compound encompassed in the present invention, preferred examples of the substituent of include a halogen atom, cyano, nitro, $C_{1-4}$ alkyl, and $C_{1-4}$ haloalkyl, and more preferred examples thereof include a fluorine atom, a chlorine atom, a bromine atom, an iodine atom, cyano, nitro, methyl, ethyl, and trifluoromethyl. At this time, when n is an integer of 2, Ys may be the same as or different from each other.

In the compound encompassed in the present invention, preferred examples of n that, is the number of substituents of Y include 0 to 2.

In the compound encompassed in the present invention, preferred examples of the substituent of $R^1$ include methyl, ethyl, n-propyl, isopropyl, difluoromethyl, chlorodifluoromethyl, bromodifluoromethyl, trifluoromethyl, cyclopropyl, dichlorocyclopropyl, dibromocyclopropyl, and difluorocyclopropyl, and more preferred examples thereof include chlorodifluoromethyl, bromodifluoromethyl, and trifluoromethyl.

In the compound encompassed in the present invention, preferred examples of the substituent of L include a chlorine atom, a bromine atom, an iodine atom, methanesulfonyloxy, trifluoromethanesulfonyloxy, benzenesulfonyloxy, para-toluenesulfonyloxy, —C(O)OH, —C(O)OR$^{10}$, and —C(O)J, and more preferred examples thereof include a chlorine atom, a bromine atom, an iodine atom, trifluoromethanesulfonyloxy, —C(O)OH, and —C(O)Cl.

In the compound encompassed in the present invention, preferred examples of the substituent of $R^2$ include a hydrogen atom, cyano, methyl, ethyl, trifluoromethyl, and 2,2,2-trifluoroethyl, and more preferred examples thereof include a hydrogen atom and methyl.

In the compound encompassed in the present invention, preferred examples of the substituent of $R^3$ include a hydrogen atom, methyl, and ethyl, and more preferred examples thereof include a hydrogen atom and methyl.

In the compound encompassed in the present invention, preferred examples of the substituent of $R^4$ include $C_{1-6}$ alkyl, $C_{1-6}$ alkyl arbitrarily substituted with $R^{11}$, $C_{1-6}$ haloalkyl, $C_{3-8}$ cycloalkyl, $C_{3-8}$ halocycloalkyl, $C_{3-6}$ alkenyl, $C_{3-6}$ haloalkenyl, phenyl, and phenyl substituted with $(Z)_t$, and more preferred examples thereof include methyl, ethyl, n-propyl, isopropyl, cyanomethyl, methoxyethyl, ethoxyethyl, methylthioethyl, methanesulfonylethyl, cyclopropylmethyl, 2,2-dichlorocyclopropylmethyl, 2-fluoroethyl, 2-chloroethyl, 2-bromoethyl, 2,2,2-trifluoroethyl, 2,2,2-trichloroethyl, 2-propenyl, 3,3-difluoro-2-propenyl, 3,3-dichloro-2-propenyl, and 2-propynyl.

In the compound encompassed in the present invention, preferred examples of the substituent of $R^5$ include a hydrogen atom, methyl, ethyl, —CHO, acetyl, propionyl, methoxycarbonyl, ethoxycarbonyl, and methanesulfonyl, and more preferred examples thereof include a hydrogen atom, methyl, acetyl, propionyl, and methoxycarbonyl.

In the compound encompassed in the present invention, preferred examples of the substituent of $R^6$ include $C_{1-4}$ alkyl, $C_{1-4}$ haloalkyl, and $C_{1-4}$ alkoxy($C_{1-4}$)alkyl, and more preferred examples thereof include methyl, ethyl, trifluoromethyl, trifluoroethyl, methoxymethyl, ethoxymethyl, and methoxyethyl.

In the compound encompassed in the present invention, preferred examples of the substituent of $R^7$ include —CHO, $C_{1-4}$ alkylcarbonyl, and $C_{1-4}$ alkoxycarbonyl, and more preferred examples thereof include formyl, acetyl, propionyl, methoxycarbonyl, and ethoxycarbonyl.

In the compound encompassed in the present invention, preferred examples of the substituent of $R^8$ include a hydrogen atom, methyl, and ethyl.

In the compound encompassed in the present invention, preferred examples of the substituent of $R^9$ include methyl, ethyl, trifluoromethyl, trifluoroethyl, phenyl, and phenyl substituted with $(Z)_t$, and more preferred examples thereof include methyl, trifluoromethyl, and para-methylphenyl.

In the compound encompassed in the present invention, preferred examples of the substituent of $R^{10}$ include $C_{1-6}$ alkyl, $C_{1-4}$ alkoxy($C_{1-4}$)alkyl, $C_{1-6}$ haloalkyl, benzyl, phenyl, and phenyl substituted with $(Z)_t$, and more preferred examples thereof include methyl, ethyl, n-propyl, isopropyl, n-butyl, isobutyl, sec-butyl, tert-butyl, 2-chloroethyl, 2-bromoethyl, 2-methoxyethyl, benzyl, and phenyl.

In the compound encompassed in the present invention, preferred examples of the substituent of $R^{11}$ include cyano, $C_{3-8}$ cycloalkyl, $C_{3-8}$ halocycloalkyl, $—OR^6$, $—S(O)_rR^6$, and $—N(R^8)R^7$, and more preferred examples thereof include cyano, cyclopropyl, cyclobutyl, difluorocyclopropyl, dichlorocyclopropyl, $—OR^6$, and $—S(O)_rR^6$.

In the compound encompassed the present invention, preferred examples of the substituent of Z include a halogen atom, cyano, nitro, $C_{1-6}$ alkyl, $C_{1-6}$ haloalkyl, $—OR^6$, $—S(O)_r R^6$, and $—N(R^8)R^7$, and more preferred examples thereof include a fluorine atom, a chlorine atom, a bromine atom, an iodine atom, cyano, nitro, methyl, ethyl, and trifluoromethyl. At this time, when t that is the number of substituents of Z is an integer of 2 or more, Zs may be the same as or different from each other.

In the compound encompassed in the present invention, preferred examples of t that is the number of substituents of Z include 1 to 3.

In the compound encompassed in the present invention, preferred examples of the substituent of J include a fluorine atom, a chlorine atom, and a bromine atom, and more preferred examples thereof include a chlorine atom.

Specific examples of the description in the present specification of [$R^3$ together with $R^2$ may form a $C_{2-5}$ alkylene chain to form together with a carbon atom to which $R^2$ and $R^3$ are bonded a 3- to 6-membered ring, and at this time, the alkylene chain may contain one oxygen atom, one sulfur atom, or one nitrogen atom], include cyclopropyl, cyclobutyl, cyclopentyl, tetrahydrofuran, tetrahydrothiophene, pyrrolidine, cyclohexane, tetrahydropyran, tetrahydrothiopyran, and piperidine. Each of these groups is selected from within the range of a specified number of each atom.

Specific examples of the description in the present specification of [$R^5$ together with $R^4$ may form a $C_{2-6}$ alkylene chain to form together with a nitrogen atom to which $R^4$ and $R^5$ are bonded a 3- to 7-membered ring, and at this time, the alkylene chain may contain one oxygen atom, one sulfur atom, or one nitrogen atom and may arbitrarily be substituted with an oxo group or a thioxo group],
include aziridine, azetidine, azetidine-2-one, pyrrolidine, pyrrolidine-2-one, oxazolidine, oxazolidine-2-one, oxazolidine-2-thione, thiazolidine, thiazolidine-2-one, thiazolidine-2-thione, imidazolidine, imidazolidine-2-one, imidazolidine-2-thione, piperidine, piperidine-2-one, piperidine-2-thione, 2H-3,4,5,6-tetrahydro-1,3-oxazine-2-one, 2H-3,4,5,6-tetrahydro-1,3-oxazine-2-thione, morpholine, 2H-3,4,5,6-tetrahydro-1,3-thiazine-2-one, 2H-3,4,5,6-tetrahydro-1,3-thiazine-2-thione, thiomorpholine, perhydropyrimidine-2-one, piperazine, homopiperidine, homopiperidine-2-one, and heptamethyleneimine. Each of these groups is selected from within the range of a specified number of each atom.

In the reaction of the present invention, a solvent may be used or not used. However, when the solvent is used, examples thereof include: aromatic hydrocarbons such as benzene, toluene, and xylene; aliphatic hydrocarbons such as hexane and heptane; alicyclic hydrocarbons such as cyclohexane; aromatic halogenated hydrocarbons such as chlorobenzene and dichlorobenzene; aliphatic halogenated hydrocarbons such as dichloromethane, chloroform, carbon tetrachloride, 1,2-dichloroethane, 1,1,1-trichloroethane, trichloroethylene, and tetrachloroethylene; nitriles such as acetonitrile and propionitrile; esters such as ethyl acetate, n-butyl acetate, and ethyl propionate; ethers such as diethyl ether, dimethoxyethane, tert-butyl methyl ether, methyl cyclopentyl ether, tetrahydrofuran, and 1,4-dioxane; amides such as N,N-dimethylformamide, N,N-dimethylacetamide, and N-methyl-2-pyrrolidone; dimethyl sulfoxide; 1,3-dimethyl-2-imidazolidinone; and water. These solvents may be used individually or in combination of two or more types thereof.

When a solvent is used in the reaction of the present invention, the used amount thereof is 0.2 to 50 parts by weight, preferably 0.5 to 20 parts by weight, relative to 1 part by weight of a compound of Formula (3) as a raw material.

When a base is used in the reaction of the present invention, examples of the base include: hydroxides of an alkali metal such as sodium hydroxide and potassium hydroxide; carbonates of an alkali metal such as sodium carbonate and potassium carbonate; bicarbonates of an alkali metal such as sodium hydrogen carbonate and potassium hydrogen carbonate; organic bases such as triethylamine, tributylamine, diisopropylethylamine, N,N,N',N'-tetramethylethylenediamine, N,N-dimethylaniline, pyridine, 5-ethyl-2-methylpyridine, 4-(dimethylamino)pyridine, 1,8-diazabicyclo[5,4,0]-7-undecene, and 1,4-diazacyclo[2,2,2]octane; alkali metal organic acid salts such as sodium acetate and potassium acetate; and alkali metal alkoxides such as sodium methoxide, sodium ethoxide, and potassium tert-butoxide. These bases may be used individually or in combination of two or more types thereof.

The used amount of the base used in the reaction of the present invention is 0.1 to 20 times mol, preferably 0.3 to 5 times mol, relative to 1 mol of a compound of Formula (3) as a raw material.

When a palladium compound is used in the reaction of the present invention, examples thereof include metal palladium, supported palladium, palladium salts, and palladium complexes. Although these palladium compounds may be used in combination with a ligand, in the case of a palladium complex, it is not necessary to use a ligand. Examples of the supported palladium include palladium supported on activated carbon, palladium supported on alumina, palladium supported on zeolite, and palladium supported on perovskite oxide, and examples of the palladium salt include palladium chloride, palladium bromide, and palladium acetate. Examples of the palladium complex include tetrakis(triphenylphosphine)palladium, [bis(triphenylphosphine)]palladium chloride, [bis(triphenylphosphine)]palladium acetate, [1,4-bis(diphenylphosphino)propane]palladium chloride, [1,4-bis(diphenylphosphino)butane]palladium chloride, [1,4-bis(acetonitrile)]palladium chloride, [1,4-bis(benzonitrile)]palladium chloride, bis(dibenzylideneacetone)palladium, [1,3-bis(2,4,6-triphenyl)imidazole-2-ylidene(1,4-naphthoquinone)]palladium (0) dimer, [1,3-bis(2,6-diisopropylphenyl)imidazole-2-ylidene(1,4-naphthoquinone)]palladium (0) dimer, and allylchloro[1,3-bis(2,4,6-triphenyl)imidazole-2-ylidene(1,4-naphthoquinone)]palladium (II) dimer. Among them, preferred are palladium supported on activated carbon, palladium chloride, palladium acetate, [bis(triphenylphosphine)]palladium chloride, and tetrakis(triphenylphosphine) palladium.

The used amount of the palladium compound used in the reaction of the present invention is 0.00001 to 0.5 times mol, preferably 0.0001 to 0.05 times mol, relative to 1 mol of a compound of Formula (3) as a raw material.

Examples of the ligand capable of being used together with a palladium compound in the reaction of the present invention include phosphine compounds and nitrogen compounds. Examples of the phosphine compound include trimethylphosphine, triethylphosphine, triisopropylphosphine, tri-n-butylphosphine, tri-tert-butylphosphine, triphenylphosphine, tri-ortho-methylphenylphosphine, 1,3-bis(dimethylphosphino)propane, 1,2-bis(diphenylphosphino)ethane, 1,3-bis(diphenylphosphino)propane, 1,4-bis(diphenylphosphino)butane, and 1,1'-bis(diphenylphosphino)ferrocene. Examples of the nitrogen compound include tetramethylethylenediamine, pyridine, 1,10-phenanthroline, and 2,9-dimethyl-1,10-phenanthroline. Among them, preferred are tri-tert-butylphosphine, triphenylphosphine, 1,2-bis(diphenylphosphino)ethane, 1,3-bis(diphenylphosphino)propane, 1,4-bis(diphenylphosphino)butane, and 1,1'-bis(diphenylphosphino)ferrocene.

When the ligand is used, the used amount thereof is 0.5 to 100 times mol, preferably 1 to 10 time(s) mol, relative to 1 mol of palladium in the used palladium compound.

Carbon monoxide may be sot in an arbitrary pressure range of atmospheric, pressure to 5 MPa, preferably atmospheric pressure to 1 MPa.

In the reaction of the present invention, although a phase-transfer catalyst may be used or not used, when the phase-transfer catalyst is used, examples thereof include quaternary ammonium salts, pyridinium compounds, and crown ether compounds. Examples of the quaternary ammonium salt include tetramethylammonium chloride, tetramethylammonium bromide, tetramethylammonium iodide, tetramethylammonium hydroxide, tetramethylammonium acetate, tetraethylammonium chloride, tetraethylammonium bromide, tetramethylammonium iodide, tetraethylammonium hydroxide, tetrabutylammonium chloride, tetrabutylammonium bromide, tetrabutylammonium iodide, tetrabutylammonium hydroxide, trimethylbenzylammonium chloride, trimethylbenzylammonium bromide, trimethylbenzylammonium iodide, trimethylbenzylammonium hydroxide, triethylbenzylammonium chloride, triethylbenzylammonium bromide, triethylbenzylammonium triethylbenzylammonium hydroxide, triethylmethylammonium chloride, trimethylammonium bromide, triethylmethylammonium iodide, triethylmethylammonium hydroxide, trimethylethylammonium chloride, trimethylethylammonium bromide, trimethylethylammonium iodide, trimethylethylammonium hydroxide, methyltributylammonium chloride, methyltributylammonium bromide, methyltributylammonium iodide, methyltributylammonium hydroxide, methyltrioctylammonium chloride, methyltrioctylammonium bromide, methyltrioctylammonium iodide, methyltrioctylammonium hydroxide, hexadecyltrimethylammonium chloride, hexadecyltrimethylammonium bromide, and hexadecyltrimethylammonium hydroxide. Examples of the pyridinium compound include butylpyridinium chloride, butylpyridinium bromide, hexadecylpyridinium chloride, and hexadecylpyridinium bromide. Examples of the crown ether compound include 15-crown 5-ether, 18-crown 6-ether, and dibenzo-18-crown 6-ether. Among them, preferred are tetramethylammonium chloride, tetramethylammonium bromide, tetrabutylammonium chloride, tetrabutylammonium bromide, methyltrioctylammonium chloride, hexadecyltrimethylammonium chloride, and hexadecyltrimethylammonium bromide.

When the phase-transfer catalyst is used, the used amount thereof is 0.001 to 0.8 times mol, preferably 0.01 to 0.5 times mol, relative to 1 mol of a compound of Formula (3) as a raw material.

When a condensing agent is used in the reaction of the present invention, examples thereof include N,N'-dicyclohexylcarbodiimide, N,N'-diisopropylcarbodiimide, 1-ethyl-3-(3-dimethylaminopropyl)carbodiimide hydrochloride, 1-hydroxybenzotriazole, 1H-benzotriazole-1-yl oxytris(dimethylamino)phosphonium hexafluorophosphate, O-(benzotriazole-1-yl)-N,N,N',N'-tetramethyluronium hexafluorophosphate, 1H-benzotriazole-1-yl oxytripyrrolidinophosphonium hexafluorophosphate, 1-ethoxycarbonyl-2-ethoxy-1,2-dihydroquinoline, methyl chloroformate, ethyl chloroformate, n-propyl chloroformate, isopropyl chloroformate, tert-butyl chloroformate, isobutyl chloroformate, N,N-dimethylsulfamoyl chloride, 4-(4,6-dimethoxy-1,3,5-triazine-2-yl)-4-methylmorpholinium chloride, pivaloyl chloride, N,N-dimethylimidazolinium chloride, cyanide diethylphosphate, azide diphenylphosphate, 1,1'-carbonylbis-1H-imidazole, and 3,4-dihydro-3-hydroxy-4-oxo-1,2,3-benzotriazine.

When the condensing agent is used, the used amount thereof is 0.5 to 10 times mol, preferably 0.5 to 5 times mol, relative to 1 mol of a compound of Formula (3) as a raw material.

The reaction temperature may be set in an arbitrary temperature range of −20 to 200° C., preferably −10 to 150° C.

The reaction time varies depending on the type of the reaction, the concentration of the reaction substrate, the reaction temperature, the reaction scale, and the like. However, the reaction time may arbitrarily be set in a range of 5 minutes to 100 hours.

Although the compound of Formula (1-1) in the present specification includes optically active substances due to the presence of one asymmetric carbon atom, the present specification relates to a racemic body.

In the crystallization or the phase transition of the present specification, a compound (1-1) used as a raw material may be in any form such as a crystal polymorph including pseudo polymorph, an amorphous, a mixture thereof; and a solution.

The racemic body of the compound of Formula (1-1) of the present specification includes a I-form crystal, a II-form crystal, a III-form crystal, and an amorphous substance.

In the I-form crystal, the diffraction angle (2θ) in the powder X-ray diffraction spectrum has peaks at 4.4°, 8.7°, 11.1°, 13.1°, 14.4°, 14.8°, 16.3°, 16.9°, 17.4°, 17.7°, 18.1°, 18.8°, 19.4°, 21.2°, 21.9°, 22.3°, 23.0°, 23.9°, 24.5°, 25.0°, 26.3°, and 27.3°, or the powder X-ray diffraction spectrum thereof has substantially the same pattern as that of the powder X-ray diffraction spectrum exemplified in FIG. 1.

The DSC measurement thereof has a peak top at 173 to 176° C.

Figure 2:
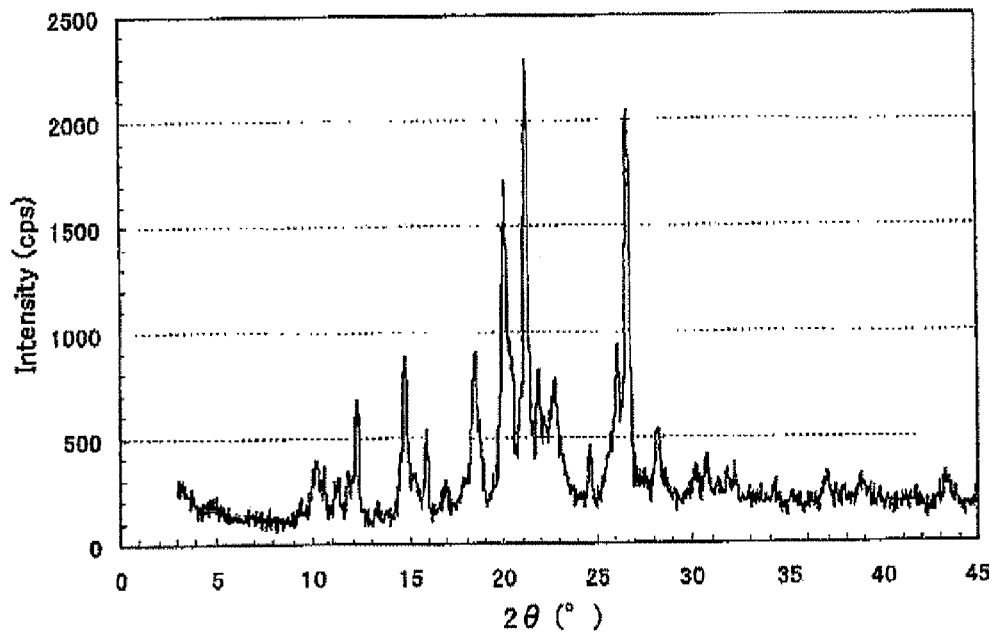
FIG. 2 shows a powder X-ray diffraction pattern of a II-form crystal of a compound of Formula (1-1).

In the II-form crystal, the diffraction angle (2θ) in the powder X-ray diffraction spectrum has peaks at 10.2°, 12.3°, 14.7°, 15.9°, 18.4°, 20.1°, 21.2°, 22.0°, 22.8°, 24.6°, and 26.6°, or the powder X-ray diffraction spectrum thereof has substantially the same pattern as that of the powder X-ray diffraction spectrum exemplified in FIG. 2.

The DSC measurement thereof has a peak top at 169 to 174° C.

Figure 3:
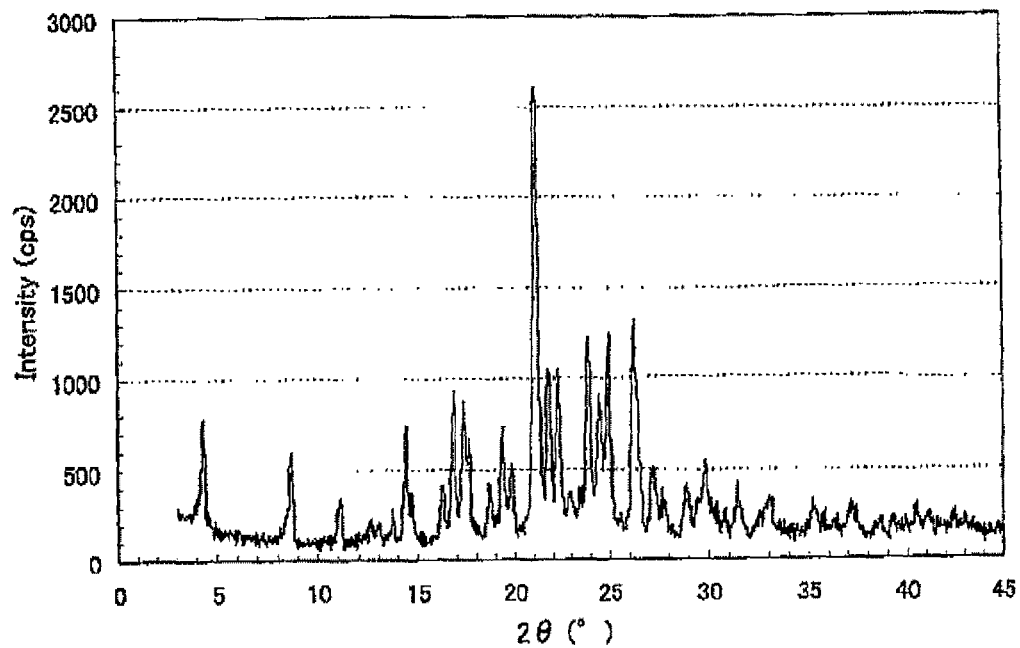
FIG. 3 shows a powder X-ray diffraction pattern of a III-form crystal of a compound of Formula (1-1).

In the III-form crystal, the diffraction angle (2θ) in the powder X-ray diffraction spectrum has peaks at 4.3°, 8.7°, 11.1°, 14.4°, 16.3°, 16.9°, 17.4°, 17.7°, 18.7°, 19.4°, 19.9°, 21.2°, 21.8°, 22.3°, 23.8°, 24.4°, 24.9°, and 26.2°, or the powder X-ray diffraction spectrum thereof has substantially the same pattern as that of the powder X-ray diffraction spectrum exemplified in FIG. 3.

In the DSC measurement thereof, a peak at around 167° is detected as a shoulder of an endothermic peak having a peak top at around 172° C.

Figure 4:
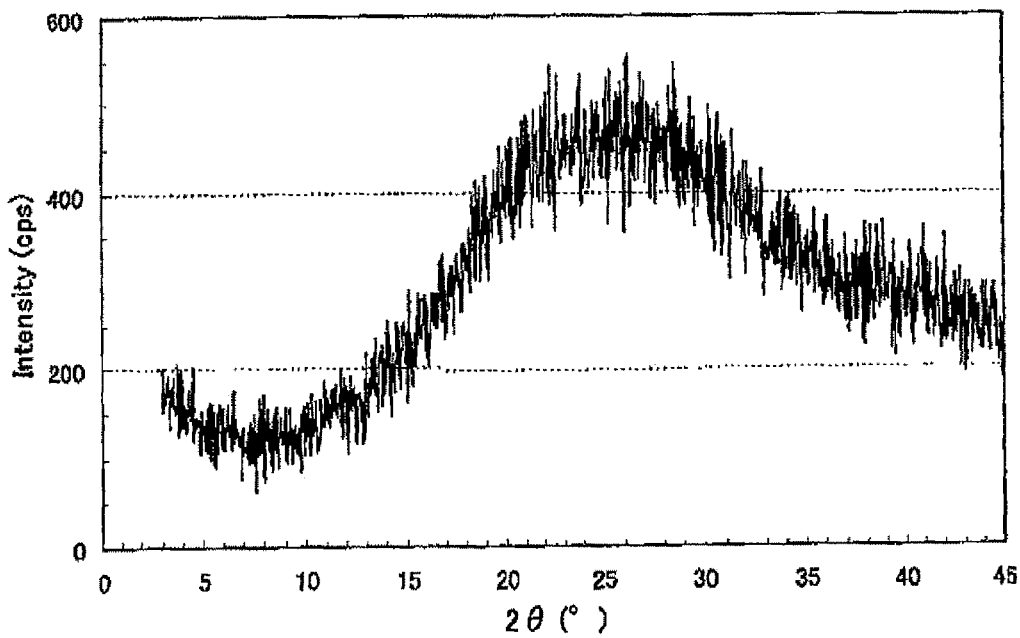
FIG. 4 shows a powder X-ray diffraction pattern of an amorphous substance of a compound of Formula (1-1).

The amorphous substance has substantially the same pattern as that of the powder X-ray diffraction spectrum exemplified in FIG. 4 and has no diffraction peak.

Next, the production method of each crystal form is described.

The I-form crystal can be produced by, for example, gradually cooling clown a solution of a compound of Formula (1-1) in a saturated state at a high temperature to precipitate a crystal.

The II-form crystal can be produced by, for example, precipitating the crystal from a hydrous organic solution of a compound of Formula (1-1) under a stationary condition. As the hydrous organic solution, for example a solvent mixture of tetrahydrofuran and water is preferred.

The II-form crystal can also be produced by transferring another crystal form in methanol.

The III-form crystal can be produced by, for example, rapidly precipitating the crystal from a solution containing a compound of Formula (1-1).

The amorphous substance can be produced by dropping a solution in which a compound of Formula (1-1) is dissolved in acetic acid or dimethylsulfoxide into water.

Here, the I-form crystal can also be produced by transferring the III-form crystal or by crystallizing from the amorphous substance.

The crystallization, the recrystallization, or the phase transition of the present specification may be performed using a solvent or using no solvent. However, when the solvent is used, examples thereof include organic solvents and water, and solvents may be used individually or in combination. Examples of the organic solvent include alcohols such as methanol, ethanol, propanol, isopropyl alcohol, butanol, 2-butanol, isobutyl alcohol, pentanol, isopentyl alcohol, 2-methoxyethanol, 2-ethoxyethanol, 2,2,2-trifluoroethanol, and ethylene glycol; ethers such as diethyl ether, diisopropyl ether, tetrahydrofuran, dimethoxyethane, 1,4-dioxane, methyl cyclopentyl ether, tert-butyl methyl ether, tert-butyl ethyl ether, and anisole; aromatic hydrocarbons such as benzene, xylene, toluene, cumene, and tetralin; aliphatic hydrocarbons such as pentane, hexane, cyclohexane, triethylcyclohexane, heptane, and petroleum ether; halogenated hydrocarbons such as dichloromethane, chloroform, 1,2-dichloroethane, carbon tetrachloride, and chlorobenzene; ketones such as acetone, methyl ethyl ketone, methyl butyl ketone, methyl isobutyl ketone, and hexanone; esters such as ethyl formate, methyl acetate, ethyl acetate, propyl acetate, isopropyl acetate, butyl acetate, and ethyl propionate; nitriles such as acetonitrile and propionitrile; amides such as formamide, N,N-dimethylformamide, N,N-dimethylacetamide, and N-methyl-2-pyrrolidone; sulfoxides such as dimethylsulfoxide and diethylsulfoxide; sulfones such as dimethylsulfone, diethylsulfone, and sulfolan; organic acids such as formic acid and acetic acid; pyridine; nitromethane; and 1,3-dimethyl-2-imidazolidinone. These organic solvents may be used individually or in combination of two or more types thereof.

The hydrous organic solvent described in the present specification refers to a solvent mixture of the above organic solvent and water, and preferred examples of the used organic solvent include alcohols, ethers, ketones, and esters. More preferred examples thereof include methanol, ethanol, propanol, isopropyl alcohol, 2-methoxyethanol, 2-ethoxyethanol, tetrahydrofuran, dimethoxyethane, 1,4-dioxane, acetone, methyl ethyl ketone, ethyl formate, methyl acetate, ethyl acetate, and butyl acetate, and more preferred examples thereof include methanol, tetrahydrofuran, and ethyl acetate.

Examples of the method for rapidly precipitating a crystal described in the present specification include a method of quenching a solution in which a compound of Formula (1-1) is dissolved in an organic solvent, and a method of dropping a solution containing a compound of Formula (1-1) into a poor solvent. Preferred examples of the organic solvent include organic solvents except dimethylsulfoxide and acetic acid, and examples of the poor solvent include the above-described aromatic hydrocarbons, aliphatic hydrocarbons, and halogenated hydrocarbons, and water. Among them, preferred are toluene, cumene, tetralin, pentane, hexane, cyclohexane, methylcyclohexane, heptane, dichloromethane, chloroform, 1,2-dichloroethane, and water, and more preferred are toluene, hexane, heptane, and water.

The peak represented by a characteristic diffraction angle ($2\theta$) in the powder X-ray diffraction described in the present specification may vary according to the measuring conditions. Therefore, the peak of the powder X-ray diffraction described in the present specification is not to be strictly interpreted.

[Conditions for Powder X-Ray Diffraction Measurement]
Apparatus: MXLabo (manufactured by Mac Science Co., Ltd. (at present, Bruker AXS K.K.))
Ray source: Cu
Wavelength: 1.54056 A
Goniometer: upright goniometer
Tube voltage: 40.0 kV
Tube current 30 mA.
Measuring method: continuous method
Data range: 3.0400 to 45.0000 deg
Scanning axis: $2\theta/\theta$
Sampling interval: 0.0400 deg
Scanning rate: 8.000 deg/min.
Diffusion slit: 1.00 deg
Scattering slit: 1.00 deg
Light receiving slit; 0.15 mm
RSM: 0.8 mm The I-form crystal, the II-form crystal, the III-form crystal, or the amorphous substance of the compound (1-1) of the present invention can effectively control, with a low concentration thereof, any pests such as: insects including so-called agricultural insect pests damaging agricultural or horticultural crops and trees or the like, so-called domestic animal insect pests being parasitic in domestic animals/fowls, so-called sanitary insects adversely affecting, in various manners, the living environment of the human such as the house, and so-called stored grain insect pests damaging grains and the like stored in warehouses; and mites, Crustacea, Mollusca, and Nematoda that are generated and cause damages in a situation similar to that in the case of the insects.

Each of the I-form crystal, the II-form crystal, the III-form crystal, and the amorphous substance of the compound of Formula (1-1) has technical characteristics such as enhancing the activity, enhancing the easiness of handling, and enhancing the preparation stability.

Specific examples of the insects, the mites, the Crustacea, the Mollusca, and the Nematoda capable of being controlled using the I-form crystal, the II-form crystal, the III-form crystal, or the amorphous substance of the compound of Formula (1-1) include:

Lepidopteran insects such as *Adoxophyes bonmai, Adoxophyes orana faciata, Archips breviplicanus, Archips fuscocu-* preanus, Grapholita molesta, Homona magnanima, Leguminivora glycinivorella, Matsumuraeses phaseoli, Pandemis heparana, Bucculatrix privorella, Lyonetia clerkella, Lyonetia prunifoliella malinella, Caloptilia theivora, Phyllonorycter ringoniella, Phyllocnistis citrella, Acrolepiopsis sapporensis, Acrolepiopsis suzukiella, Plutella xylostella, Stathmopoda masinissa, Helcystogramma triannulella, Pectinophora gossypiella, Carposina sasakii, Cydla pomonella, Chilo suppressalis, Cnaphalocrocis medinalis, Conogethes punctiferalis, Diaphania indica, Etiella zinekenella, Glyphodes pyloalis, Hellula undalis, Ostrinia furnacalis, Ostrinia scapulais, Ostrinia nubilalis, Parapediasia teterrella, Parnara guttata, Pieris brassicae, Pieris rapae crucivora, Ascotis selenaria, Pseudoplusia includens, Euproctis pseudoconspersa, Lymantria dispar, Orgyia thyellina, Hyphantria cunea, Lernyra imparilis, Adris tyrannus, Aedia leucomelas, Agrotis ipsilon, Agrotis segetum, Autographa nigrisigna, Ctenoplusia agnata, Helicoverpa armigera, Helicoverpa assulta, Helicoverpa zea, Heliothis virescens, Mamestra brassicae, Mythimna separata, Naranga aenescens, Spodoptera eridania, Spodoptera exigua, Spodoptera frugiperda, Spodoptera Spodoptera litura, Spodoptera depravata, Trichoplusia ni, Endopiza viteana, Manduca quinquemaculata, and Manduca sexta;

Thysanoptera insects such as Frankliniella intonsa, Frankliniella occidentalis, Heliothrips haemorrhoidalis, Scirtothrips dorsalis, Thrips palmi, Thrips tabaci, and Ponticulothrips diospyrosi;

Hemiptera insects such as Dolycoris baccarum, Eurydema rugosturt, Eysarcoris aeneus, Eysarcoris lewisi, Eysarcoris ventralis, Glaucias subpunctatus, Halyomorpha halys, Nezara antennata, Nezara viridula, Piezodorus hybneri, Plautia crossota, Scotinophora lurida, Cletus punctiger, Leptocorisa chinensis, Riptortus clavatus, Rhopalus msculatus, Cavelerius saccharivorus, Togo hernipterus, Dysdercus cingulatus, Stephanitis pyrioides, Halticus insularis, Lygus lineolaris, Stenodema sibiricum, Stenotus rubrovittatus, Trigonotylus caelestialium, Arboridia apicalis, Balclutha saltuella, Epiacanthus stramineus, Empoasca fabae, Empoasca nipponica, Empoasca onukii, Empoasca sakaii, Macrosteles striifrons, Nephotettix cinctinceps, Psuedatomoscelis seriatus, Laodelphax striatella, Nilaparvata lugens, Sogatella furcifera, Diaphorina citri, Psylla pyrisuga, Aleurocanthus spiniferus, Bemisia argentifolii, Bernisia tabaci, Dialeurodes citri, Trialeurodes vaporariorum, Viteus vitifolii, Aphis gossypii, Aphis spiraecola, Myzus persicae, Toxoptera aurantii, Drosicha corpulenta, Icerya purchasi, Phenacoccus solani, Planococcus citri, Planococcus kuraunhiae, Pseudococcus cornstocki, Ceroplastes ceriferus, Ceroplastes rubens, Aonidiella aurantii, Comstockaspis perniciosa, Fiorinia these, Pseudaonidia paeoniae, Pseudaulacaspis pentagons, Pseudaulacaspis prunicola, Unaspis euonymi, Unaspis yanonensis, and Cimex lectularius;

Coleoptera insects such as Anomala cuprea, Anomala rufocuprea, Gametis jucunda, Heptophylla picea, Popillia japonica, Lepinotarsa decemlinesta, Melanotus fortnumi, Melanotus tamsuyensis, Lasioderma serricorne, Epuraea domina, Epilachna varivestis, Epilachna vigintioctopunctata, Tenebrio molitor, Tribolium castaneum, Anoplophora malasiaca, Monochamus alternatus, Psacothea hilaris, Xylotrechus pyrrhoderus, Callosobruchus chinensis, Aulacophora femoralis, Chaetocnema concinna, Diabrotica undecimpunctata, Diabrotica virgifera, Diabrotica barbei, Oulema oryzae, Phyllotreta striolata, Psylliodes angusticollis, Rhynchites heros, Cylas formicarius, Anthonomus grandis, Echinocnemus squameus, Euscepes postfasciatus, Hypera postica, Lissohoptrus oryzophilus, Otiorhynchus sulcatus, Sitophilus granarius, Sitophilus zeamais, Sphenophorus venatus vestitus, and Paederus fuscipes;

Diptera insects such as Asphondylia yushimai, Sitodiplosis mosellana, Bactrocera cucurbitae, Bactrocera dorsalis, Ceratitis capitata, Hydrellia griseola, Drosophila suzukii, Agromyza oryzae, Chromatomyia horticola, Liriomyza bryoniae, Liriornyza chinensis, Liriomyza sativae, Liriomyza trifolii, Delia platura, Pegomya cunicularia, Rhagoletis pomonella, Mayetiola destructor, Musca domestics, Stomoxys calcitrans, Melophagus ovinus, Hypoderma bovis, Hypoderma lineatum, Oestrus ovis, Glossina palpalis (Glossina morsitans), Prosimulium yezoensis, Tabanus trigonus, Telmatoscopus albipunctatus, Leptoconops nipponensis, Culex pipiens pollens, Aedes aegypti, Aedes albopicutus, and Anopheles hyrscanus sinesis;

Hymenoptera insects such as Apethynius kuri, Athalia rosae, Arge pagana, Neodiprion sertifer, Dryocosmus kuriphilus, Eciton burchelli (Eciton schmitti), Camponotus japonicus, Vespa mandarina, Myrmecia spp., Solenopsis spp., and Monomorium pharaonis;

Orthoptera insects such as Teleogryllus emma, Gryllotalpa orientalis, Locusta migratoria, Oxya yezoensis, and Schistocerca gregaria;

Collembolan insects such as Onychiurus folsomi, Onychiurus sibiricus, and Bourletiella hortensis;

Dictyoptera insects such as Periplaneta fuliginosa, Periplaneta japonica, and Blattella germanica;

Isoptera insects such as Coptotermes formosanus, Reticulitermes speratus, and Odontotermes formosanus;

Isoptera insects such as Ctenocephalidae felis, Ctenocephalides canis, Echidnophaga gallinacea, Pulex irritans, and Xenopsylla cheopis;

Mallophaga insects such as Menacanthus stramineus and Bovicola Bovis;

Anoplura insects such as Haematopinus eurystemus, Haematopinus suis, Linognathus vituli, and Solenopotes capillatus;

Tarsonemidae such as Phytonemus pallidus, Polyphagotarsonemus latus, and Tarsonemus bilobatus;

Eupodidae such as Penthaleus erythrocephalus and Penthaleus major;

Tetranychidae such as Oligonychus shinkajii, Panonychus citri, Panonychus mori, Panonychus ulmi, Tetranychus kanzawai, and Tetranychus urticae;

Eriophyidae such as Acaphylla theavagrans, Aceria tulipae, Aculops lycopersici, Aculops pelekassi, Aculus schlechtendali, Eriophyes chibaensis, and Phyllocoptruta oleivora;

Acaridae such as Rbizoglyphus robizti, Tyrophagus putrescentiae, and Tyrophagus similis;

Varroa destructor such as Varroa jacobsoni;

Ixodidae such as Boophilus microplus, Rhipicephalus sanguineus, Haemaphysalis longicornis, Haemophysalis flava, Haemophysalis campanulata, Ixodes ovatus, Ixodes persulcatus, Amblyomma spp., and Dermacentor spp.;

Cheyletidae such as Cheyletiella yasguri and Cheyleviella blakei;

Demodicidae such as Demodex canis and Demodex cati;

Psoroptidae such as Psoroptes ovis;

Sarcoptidae such as Sarcoptes scabiei, Notoedres cati, and Knemidocoptes spp.;

Crustacea such as Armadillidium vulgare;

Gastropoda such as Pomacea canaliculata, Achatina fulica, Meghimatium bilineatum, Limax Valentina, Acusta despecta sieboldiana, and Euhadra peliomphala; and Nematoda such as Prathylenchus coffeae, Prathylenchus penetrans, Prathylenchus vulnus, Globodera rostochiensis, Heterodera glycines, Meloidogyne hapla, Meloidogyne

*incognita, Aphelenchoides besseyi,* and *Bursaphelenchtta xylophilus,* which should not be construed as limiting the scope of the present invention.

Specific examples of the internal parasites of domestic animals, fowls, pet animals, or the like capable of being controlled using the I-form crystal, the II-form crystal, the III-form crystal, or the amorphous substance of the compound of Formula (1-1) include:

Nematoda such as *Haemonchus, Trichostrongylus, Ostertagia, Nematodirus, Cooperia, Ascaris, Bunostomum, Oesophagostomum, Chabertia, Trichuris, Storongylus, Trichonema, Dietyocaulus, Capillaria, Heterakis, Toxocara, Ascaridia, Oxyuris, Ancylostoma, Uncinaria, Toxascaris,* and *Parascaris;*

Nematoda, Filariidae such as *Wuchereria, Brugia, Onchoceca, Dirofilaria,* and *Loa;*

Nematoda, Dracunculidae such as *Deacunculus;*

Cestoda such as *Dipylidium caninum, Taenia taeniaeformis, Taenia solium, Taenia saginata, Hymenolepis diminuta, Moniezia benedeni, Diphyllobothrium latum, Diphyllobothrium erinacei, Echinococcus granulosus,* and *Echinococcus multilocularis;*

Trematoda such as *Fasciola hepatica* and *F. gigantica, Paragonimus westermanii, Fasciolopsic bruski, Eurytrema pancreaticum* and *E. coelomaticum, Clonorchis sinensis, Schistosoma japonicum, Schistosoma haematobium,* and *Schistosoma mansoni;*

*Eimeria* spp. such as *Eimeria tenella, Eimeria acervulina, Eimeria brunetti, Eimeria maxima, Eimeria necatrix, Eimeria bovis,* and *Eimeria ovinoidalis;*

*Trypanosomsa cruzi; Leishmania* spp.; *Plasmodium* spp.; *Babesis* spp.; *Trichomonadidae* spp.; *Histomanas* spp.; *Giardia* spp.; *Toxoplasma* spp.; *Entamoeba histolytica;* and *Theileria* spp, which should not be construed as limiting the scope of the present invention.

Furthermore, the I-form crystal, the II-form crystal, the III-form crystal, or the amorphous substance of the compound of Formula (1-1) is effective against pests that have developed the resistance to the conventional insecticides such as organic phosphorus-based compounds, carbamate-based compounds, or pyrethroid-based compounds.

That is, the I-form crystal, the II-form crystal, the III-form crystal, or the amorphous substance of the compound of Formula (1-1) can effectively control pests belonging to insects such as *Collembola, Dictyoptera (Blattaria), Orthoptera, Isoptera, Thysanoptera, Hemiptera (Heteroptera* and *Homoptera), Lepidoptera,* Coleoptera, *Hymenoptera,* Diptera, *Isoptera (Siphonaptera),* and *Pfrthiraptera;* mites; Gastropoda; and Nematoda, with a low concentration. On the other hand, the compound of the present invention has an extremely useful characteristic of having substantially no adverse effect on mammals, fish, Crustacea, and beneficial insects (useful insects such as Apidae and Bombus, and natural enemies such as *Aphelinidae, Aphidiidae, Tachinidae, Orius,* and *Amblyseius*).

Besides the I-form crystal, the II-form crystal, the III-form crystal, or the amorphous substance of the compound of Formula (1-1), one or more type(s) of publicly known agricultural chemical such as a herbicide, an insecticide, a miticide, a nematicide, an antiviral drug, a plant growth regulator, a fungicide, a synergist, an attractant, and a repellent may further be contained, and in this case, even more excellent control effect may be exhibited. Particularly preferred examples of the publicly known agricultural chemical include a fungicide, a bactericide, a nematicide, a miticide, and an insecticide. Specific examples of the general names thereof include the following names.

Fungicides: acibenzolar, ampropylos, anilazine, azaconazole, azoxystrobin, benalaxyl, benodanil, benomyl, benzamacril, binapacryl, biphenyl, bitertanol, bethoxazine, bordeaux mixture, blasticidin-S, bromoconazole, bupirimate, buthiobate, calcium polysulfide, captafol, captan, copper oxychloride, carpropamid, carbendazim, carboxin, chinomethionat, chlobenthiazone, chlorfenazol, chloroneb, chlorothalonil, chlozolinate, cufraneb, cymoxanil, cyproconazol, cyprodinil, cyprofuram, debacarb, dichlorophen, dichlobutrazol, dichlofluanid, diclomezine, dicloran, diethofencarb, diclocymet, difenoconazole, diflumetorim, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadone, fenarimol, febuconazole, fenfuram, fenpiclonil, fenpropidin, fenpropimorph, fentin, ferbam, ferimzone, fluazinam, fludioxonil, fluoroimide, fluquinconazole, flusilazole, flusulfamide, flutolanil, flutriafol, folpet, fosetyl-aluminium, fuberidazole, furalaxyl, fenamidone, fenhexamid, guazatine, hexachlorobenzene, hexaconazole, hymexazol, imazalil, imibenconazole, iminoctadine, ipconazole, iprobenfos, iprodione, isoprothiolane, iprovalicarb, kasugamycin, kresoxim-methyl, mancopper, mancozeb, maneb, mepanipyrim, mepronil, metalaxyl, metconazole, metiram, metominostrobin, myclobutanil, nabam, nickel bis(dimethyldithiocarbamate), nitrothal-isopropyl, nuarimol, octhilinone, ofurace, oxadixyl, oxycarboxin, oxpoconazole fumarate, pefurzoate, penconazole, pencycuron, phthalide, piperalin, polyoxins, probenazole, prochloraz, procymidone, propamocarb hydrochloride, propiconazole, propineb, pyrazophos, pyrifenox, pyrimethanil, pyroquilon, quinoxyfen, quintozene, sulfur, spiroxamine, tebuconazole, tecnazene, tetraconazole, thiabendazole, thifluzamide, thiophanate-methyl, thiram, tolclofos-methyl, tolylfluanid, triadimefon, toriadimenol, triazoxide, tricyclazole, tridemorph, triflumizole, triforine, triticonazole, validamycin, vinclozolin, zineb, ziram, and oxine-copper.

Bactericides: streptomycin, oxytetracycline, and oxolinic acid.

Nematicides: aldoxycarb, fosthiazate, fosthietan, oxamyl, and fenamiphos.

Miticides: amitraz, bromopropylate, chinomethionat, chlorobenzilate, clofentezine, cyhexatine, dicofol, dienochlor, etoxazole, fenazaquin, fenbutatin oxide, fenpropathrin, fenproximate, halfenprox, hexythiazox, milbemectin, propargite, pyridaben, pyrimidifen, and tebufenpyrad.

Insecticides: abamectin, acephate, acetamipirid, azinphosmethyl, bendiocarb, benfuracarb, bensultap, bifenthrin, buprofezin, butocarboxim, carbaryl, carbofuran, carbosulfan, cartap, chlorfenapyr, chlorpyrifos, chlorfenvinphos, chlorfluazuron, clothianidin, chromafenozide, chlorpyrifos-methyl, cyfluthrin, beta-cyfluthrin, cypermethrin, cyromazine, cyhalothrin, lambda-cyhalothrin, deltamethrin, diafenthiuron, diazinon, diacloden, diflubenzuron, dimethylvinphos, diofenolan, disulfoton, dimethoate, EPN, esfenvalerate, ethiofencarb, ethiprole, etofenprox, etrimfos, fenitrothion, fenobucarb, fenoxycarb, fenpropathrin, fenvalerate, fipronil, flucythrinate, flufenoxuron, flufenprox, tau-fluvalinate, fonophos, formetanate, formothion, furathiocarb, halofenozide, hexaflumuron, hydramethylnon, imidacloprid, isofenphos, indoxacarb, isoprocarb, isoxathion, lufenuron, malathion, metaldehyde, methamidophos, methidathion, methacrifos, metalcarb, methomyl, methoprene, methoxychlor, methoxyfenozide, monocrotophos, muscalure, nitenpyram, omethoate, oxydemeton-methyl, oxamyl, parathion, parathion-methyl, permethrin, phenthoate, phoxim, phorate, phosalone, phosmet, phosphamidon, pirimicarb, pirimiphos-methyl, profenofos, pymetrozine, pyraclofos, pyriproxyfen, rotenone, sulprofos, silafluofen, spinosad, sulfotep, tebfenozide, teflubenzuron, tefluthorin, terbufos, tetrachlorvinphos, thiodicarb, thiamethoxam, thiofanox, thiometon, tolfenpyrad, tralomethrin, trichlorfon, triazuron, triflumuron, and vamidothion.

For using the I-form crystal, the II-form crystal, the III-form crystal, or the amorphous substance of the compound of Formula (1-1), the compound can be put to practical use as a preparation in any dosage form such as a soluble concentrate, an emulsifiable concentrate, a wettable powder, a water soluble powder, a water dispersible granule, a water soluble granule, a suspension concentrate, a concentrated emulsion, a suspoemulsion, a microemulsion, a dustable powder, a granule, a tablet, and an emulsifiable gel, typically by mixing the compound with an appropriate solid carrier or an appropriate liquid carrier, and further if desired by adding to the resultant mixture, a surfactant, a penetrant, a spreader, a thickener, an antifreezing agent, a binder, an anticaking agent, a disintegrant, an antifoamer, an antiseptic, or a stabilizer. From the viewpoint of laborsaving and safety improvement, the compound can be put to use by encapsulating the above preparation in any dosage form in a water soluble packaging material such as a water soluble capsule and a bag of a water soluble film.

Examples of the solid carrier include: natural mineral matters such as quartz, calcite, sepiolite, dolomite, chalk, kaolinite, pyrophyllite, sericite, halloysite, meta-halloysite, kibushi clay, gairome clay, pottery stone, Zeeklite, allophone, Shirasu, mica, talc, bentonite, activated clay, acid clay, pumice, attapulgite, zeolite, and diatom earth; burned products of natural mineral matters such as burned clay, perlite, Shirasu balloon, vermiculite, attapulgus clay, and burned diatom earth; inorganic salts such as magnesium carbonate, calcium carbonate, sodium carbonate, sodium hydrogen carbonate, ammonium sulfate, sodium sulfate, magnesium sulfate, diammonium hydrogen phosphate, ammonium dihydrogen phosphate, and potassium chloride; saccharides such, as glucose, fructose, sucrose, and lactose; polysaccharides such as starch, powdered cellulose, and dextrin; organic substances such as urea, urea derivatives, benzoic acid, and salts of benzoic acid; plants such as wood flour, cork flour, corncob, walnut shell, and tobacco stem; fly ash; white carbon (such as hydrous synthetic silica, anhydrous synthetic silica, and hydrous synthetic silicate); and fertilizers.

Examples of the liquid carrier include: aromatic hydrocarbons such as xylem, alkyl ($C_9$, $C_{10}$, or the like) benzene, phenylxylylethane, and alkyl ($C_1$, $C_3$, or the like) naphthalene; aliphatic hydrocarbons such as machine oil, n-paraffin, isoparaffin, and naphthene; a mixture of aromatic hydrocarbons and aliphatic hydrocarbons such as kerosene; alcohols such as ethanol, isopropanol, cyclohexanol, phenoxyethanol, and benzyl alcohol; polyalcohols such as ethylene glycol, propylene glycol, diethylene glycol, hexylene glycol, polyethylene glycol, and polypropylene glycol; ethers such as propyl cellosolve, butyl cellosolve, phenyl cellosolve, propylene glycol monomethyl ether, propylene glycol monoethyl ether, propylene glycol monopropyl ether, propylene glycol monobutyl ether, and propylene glycol monophenyl ether; ketones such as acetophenone, cyclohexanone, and γ-butyrolactone; esters such as aliphatic acid methyl esters, succinic acid dialkyl esters, glutamic acid dialkyl esters, adipic acid dialkyl esters, and phthalic acid dialkyl esters; acid amides such as N-alkyl ($C_1$, $C_8$, $C_{12}$, or the like) pyrrolidone; oils and fats such as soybean oil, linseed oil, rapeseed oil, coconut oil, cottonseed oil, and castor oil; dimethyl sulfoxide; and water.

These solid and liquid carriers may be used individually or in combination of two or more types thereof.

Examples of the surfactant include the following (A), (B), (C), (D), and (E).

(A) Nonionic Surfactants:

(A-1) Polyethylene glycol surfactants: for example, a polyoxyethylene alkyl (for example, $C_{8-18}$) ether, an alkylnaphthol ethylene oxide adduct, a polyoxyethylene (mono- or di-) alkyl (for example, $C_{8-12}$) phenyl ether, a polyoxyethylene (mono- or di-) alkyl (for example, $C_{8-12}$) phenyl ether formalin condensate, a polyoxyethylene (mono-, di- or tri-) phenyl phenyl ether, a polyoxyethylene (mono-, di-, or tri-) benzyl phenyl ether, a polyoxypropylene (mono-, di-, or tri-) benzyl phenyl ether, a polyoxyethylene (mono-, di-, or tri) styryl phenyl ether, a polyoxypropylene (mono-, di-, or tri-) styryl phenyl ether, a polymer of a polyoxyethylene (mono-, di-, or tri) styryl phenyl ether, a polyoxyethylene polyoxypropylene (mono-, di-, or tri-) styryl phenyl ether, a polyoxyethylene polyoxypropylene block polymer, an alkyl (for example, $C_{8-18}$) polyoxyethylene polyoxypropylene block polymer ether, an alkyl (for example, $C_{8-12}$) phenyl polyoxyethylene polyoxypropylene block polymer ether, a polyoxyethylene bisphenyl ether, an ester of a polyoxyethylene resin acid, a monoester of a polyoxyethylene aliphatic acid (for example, $C_{8-18}$), a diester of a polyoxyethylene aliphatic acid (for example, $C_{8-18}$), an ester of a polyoxyethylene sorbitan (mono-, di-, or tri-) aliphatic acid (for example, $C_{8-18}$), a glycerol aliphatic acid ester ethyleneoxide adduct, a castor oil ethyleneoxide adduct, a hardened castor oil ethyleneoxide adduct, an alkyl (for example, $C_{8-18}$) amine ethyleneoxide adduct, and an aliphatic acid (for example, $C_{8-18}$) amide ethyleneoxide adduct;

(A-2) Polyhydric alcohol surfactants: for example, a glycerol aliphatic acid ester, a polyglycerine aliphatic acid ester, a pentaerythritol aliphatic acid ester, a sorbitol aliphatic acid (for example, $C_{8-18}$) ester, a sorbitan (mono-, di-, or tri-) aliphatic acid (for example, $C_{8-18}$) ester, a sucrose aliphatic acid ester, a polyhydric alcohol alkyl ether, an alkyl glycoside, an alkyl polyglycoside, and an aliphatic acid alkanolamide.

(A-3) Acetylene surfactants; for example, an acetylene glycol, an acetylene alcohol, an acetylene glycol ethyleneoxide adduct, and an acetylene alcohol ethyleneoxide adduct.

(B) Anionic Surfactants:

(B-1) Carboxylic acid surfactants: for example, a copolymer of polyacrylic acid, polymethacrylic acid, polymaleic acid, polymaleic acid anhydride, maleic acid, or maleic anhydride with an olefin (such as isobutylene and diisobutylene), a copolymer of acrylic acid with itaconic acid, a copolymer of methacrylic acid with itaconic acid, a copolymer of maleic acid or maleic anhydride with styrene, a copolymer of acrylic acid with methacrylic acid, a copolymer of acrylic acid with methyl acrylate, a copolymer of acrylic acid with vinyl acetate, a copolymer of acrylic acid with maleic acid or maleic anhydride, a polyoxyethylene alkyl (for example, $C_{8-18}$) ether acetic acid, an N-methyl-aliphatic acid (for example, $C_{8-18}$) sarcosinate, a carboxylic acid such as a resin acid and an aliphatic acid (for example, $C_{8-18}$), and salts of these carboxylic acids.

(B-2) Sulfate ester surfactants: for example, sulfate esters such as an alkyl (for example, $C_{8-18}$) sulfate ester, a polyoxyethylene alkyl (for example, $C_{8-18}$) ether sulfate ester, a polyoxyethylene (mono- or di-) alkyl (for example, $C_{8-12}$) phenyl ether sulfate ester, a sulfate ester of a polymer of a polyoxyethylene (mono- or di-) alkyl (for example, $C_{8-12}$) phenyl ether, a polyoxyethylene (mono-, di-, or tri-) phenyl phenyl ether sulfate ester, a polyoxyethylene (mono-, di-, or tri-) benzyl phenyl ether sulfate ester, a polyoxyethylene (mono-, di-, or tri-) styryl phenyl ether sulfate ester, a sulfate ester of a polymer of a polyoxyethylene (mono-, di-, or tri-) styryl phenyl ether, a sulfate ester of a polyoxyethylene polyoxypropylene block polymer, a sulfated oil, a sulfated aliphatic acid ester, a sulfate ester of a sulfated aliphatic acid with a sulfated olefin, and salts of these sulfate esters.

(B-3) Sulfonic acid surfactants: for example, sulfonic acids such as a paraffin (for example, $C_{8-12}$) sulfonic acid, an alkyl (for example, $C_{8-12}$) benzene sulfonic acid, an alkyl (for example, $C_{8-12}$) benzene sulfonic acid formalin condensate, a cresol sulfonic acid formalin condensate, an α-olefin (for example, $C_{8-16}$) sulfonic acid, a dialkyl (for example, $C_{8-12}$) sulfosuccinic acid, lignosulfonic acid, a polyoxyethylene (mono- or di-) alkyl (for example, $C_{8-12}$) phenyl ether sulfonic acid, a polyoxyethylene alkyl (for example, $C_{8-18}$) ether sulfosuccinic acid half ester, naphthalene sulfonic acid, a (mono- or di-) alkyl (for example, $C_{8-12}$) naphthalene sulfonic acid, a naphthalene sulfonic acid formalin condensate, a (mono- or di-) alkyl (for example, $C_{1-6}$) naphthalene sulfonic acid formalin condensate, a creosote oil sulfonic acid formalin condensate, an alkyl (for example, $C_{8-12}$) diphenylether disulfonic acid, Igepon T (trade name), a polystyrene sulfonic acid, and a copolymer of styrenesulfonic acid with methacrylic acid; and salts of these sulfonic acids.

(B-4) Phosphate ester surfactants: for example, phosphate esters such as an alkyl (for example, $C_{8-12}$) phosphate ester, a polyoxyethylene alkyl (for example, $C_{8-18}$) ether phosphate ester, a polyoxyethylene (mono- or di-) alkyl (for example, $C_{8-12}$) phenyl ether phosphate ester, a phosphate ester of a polymer of a polyoxyethylene (mono-, di-, or tri-) alkyl (for example, $C_{8-12}$) phenyl ether, a polyoxyethylene (mono-, di-, or tri-) phenyl phenyl ether phosphate ester, a polyoxyethylene (mono-, di-, or tri-) benzyl phenyl ether phosphate ester, a polyoxyethylene (mono-, di-, or tri-) styryl phenyl ether phosphate ester, a phosphate ester of a polymer of a polyoxyethylene (mono-, di-, or tri-) styryl phenyl ether, a phosphate ester of a polyoxyethylene polyoxypropylene block polymer, phosphatidyl choline, phosphatidyl ethanol imine, and a condensed phosphoric acid (for example, tripolyphosphoric acid); and salts of these phosphate esters.

Examples of the counter ion of the salts in (B-1) to (B-4) above include alkali metals (such as lithium, sodium, and potassium), alkaline earth metals (such as calcium and magnesium), and ammonium and various amines (such as alkylamines, cycloalkylamines, and alkanolamines).

(C) Cationic Surfactants:

For example, an alkyl amine, an alkyl quaternary ammonium salt, an alkyl amine ethylene oxide adduct, and an alkyl quaternary ammonium salt ethylene oxide adduct.

(D) Amphoteric Surfactants:

(D-1) Betaine-type surfactants: for example, an alkyl (for example, $C_{8-18}$) dimethyl aminoacetic acid betaine, an acyl (for example, $C_{8-18}$) aminopropyldimethyl aminoacetic acid betaine, an alkyl (for example, $C_{8-18}$) hydroxysulfo betaine, and a 2-alkyl (for example, $C_{8-18}$)-N-carboxymethyl-N-hydroxyethylimidazolinium betaine.

(D-2) Amino acid-type surfactants: for example, an alkyl (for example, $C_{8-18}$) aminopropionic acid, an alkyl (for example, $C_{8-18}$) aminodipropionic acid, and an N-acyl (for example, $C_{8-18}$)-N'-carboxyethyl-N'-hydroxyethylethylenediamine.

(D-3) Amine oxide-type surfactants: for example, an alkyl (for example, $C_{8-18}$) dimethylamine oxide and an acyl (for example, $C_{8-18}$) aminopropyldimethylamine oxide.

(E) Other Surfactants:

(E-1) Silicon-based surfactants: for example, a polyoxyethylene-methylpolysiloxane copolymer, a polyoxypropylene-methylpolysiloxane copolymer, and a poly(oxyethylene-oxypropylene)-methylpolysiloxane copolymer.

(E-2) Fluorinated surfactants: for example, a perfluoroalkenylbenzenesulfonic acid salt, a perfluoroalkylsulfonic acid salt, a perfluoroalkylcarboxylic acid salt, a perfluoroalkenyl polyoxyethylene ether, a perfluoroalkyl polyoxyethylene ether, and a perfluoroalkyltrimethyl ammonium salt.

These surfactants may be used individually or in combination of two or more types thereof, and in the case where two or more types are mixed, the mixing ratio can freely be selected. Although the content of these surfactants in the composition of the present invention can accordingly be selected, the content is preferably in a range of 0.1 to 20 parts by weight, relative to 100 parts by weight of the composition of the present invention.

Although the application dosage of the I-form crystal, the II-form crystal, the III-form crystal, or the amorphous substance of the compound of Formula (1-1) varies depending on the application situation, the application period, the application method, the cultivated crop, and the like, the application dosage is generally appropriate to be around 0.005 to 50 kg per hectare (ha) as the active ingredient amount.

On the other hand, in using the I-form crystal, the II-form crystal, the III-form crystal, or the amorphous substance of the compound of Formula (1-1) for controlling external or internal parasites of mammals and birds as domestic animals and pet animals, an effective amount of the I-form crystal, the II-form crystal, the III-form crystal, or the amorphous substance of the compound of Formula (1-1) can be applied together with additives for the preparation by: oral application and parenteral application such as injections (intramuscular, subcutaneous, intravenous, and intraperitoneal); a percutaneous application such as immersing, spraying, bathing, cleaning, pouring-on, and spotting-on, and dusting; and transnasal application. The compound of the present invention can also be applied to as a molded product using a strip, a plate, a band, a collar, an ear mark, a limb band, an indicator, and the like. For the application of the I-form crystal, the II-form crystal, the III-form crystal, or the amorphous substance of the compound of Formula (1-1), the compound can be prepared in any dosage form suitable for the application route.

Examples of the dosage form to be prepared include: solid preparations such as dustable powders, granules, wettable powders, pellets, tablets, boluses, capsules, and molded products containing activated compounds; soluble concentrates for injection, soluble concentrates for oral application, and soluble concentrates used on the skin or in the body cavity; solution preparations such as pour-on drugs, spot-on drugs, flowable drugs, and emulsifiable concentrates; and semisolid preparations such as ointments and gels.

The solid preparation can mainly be used for oral application, percutaneous application of the preparation diluted with water, or an environmental treatment. The solid preparation can be prepared by mixing the I-form crystal, the II-form crystal, the III-form crystal, or the amorphous substance of the compound of Formula (1-1) with an appropriate excipient, if necessary together with an adjuvant, and converting the resultant mixture into a desired form. Examples of the appropriate excipient include: inorganic substances such as carbonate salts, hydrogen carbonate salts, phosphate salts, aluminum oxide, silica, and clay; and organic substances such as saccharides, celluloses, ground grains, and starch.

The soluble concentrate for injection capable of being applied intravenously, intramuscularly, or subcutaneously can be prepared by dissolving the I-form crystal, the II-form crystal, the III-form crystal, or the amorphous substance of the compound of Formula (1-1) in an appropriate solvent, and if necessary by adding to the resultant solution, additives such as solubilizers, acids, bases, buffering salts, antioxidants, and protective agents. Examples of the appropriate solvent include water, ethanol, butanol, benzyl alcohol, glycerin, propylene glycol, polyethylene glycol, N-methylpyrrolidone, mixtures thereof, physiologically acceptable vegetable oils, and synthetic oils suitable for injection. Examples of the solubilizer include polyvinylpyrrolidone, polyoxyethylated castor oil, and polyoxyethylated sorbitan esters. Examples of the protective agent include benzyl alcohol, trichlorobutanol, p-hydroxybenzoic acid esters, and n-butanol.

The soluble concentrate for oral application can be applied directly or as a diluted soluble concentrate and can be prepared in the same manner as in the case of the soluble concentrate for injection.

The flowable drug, the emulsifiable concentrate, and the like can be applied percutaneously directly or as a diluted drug, or through an environmental treatment.

The soluble concentrate used on the skin can be applied by dropping, spreading, rubbing, atomizing, spraying, or immersing (immersing, bathing, or cleaning) to apply the drug on the skin. These soluble concentrates can be prepared in the same manner as in the case of the soluble concentrate for injection.

The pour-on drug and the spot-on drug are dropped or sprayed on a limited range of the skin, so that these drugs can immerse the I-form crystal, the II-form crystal, the III-form crystal, or the amorphous substance of the compound of Formula (1-1) into the skin to obtain the systemic effect. The pour-on drug and the spot-on drug can be prepared by dissolving, suspending, or emulsifying an active ingredient in an appropriate skin-adaptable solvent or an appropriate solvent mixture. If necessary, in these drugs, an adjuvant such as a surfactant, a colorant, an absorption-accelerating substance, an antioxidant, a light stabilizer, and an adhesive can be incorporated.

Examples of the appropriate solvent include water, alkanol, glycol, polyethylene glycol, polypropylene glycol, glycerin, benzyl alcohol, phenylethanol, phenoxyethanol, ethyl acetate, butyl acetate, benzyl benzoate, dipropylene glycol monomethyl ether, diethylene glycol monobutyl ether, acetone, methyl ethyl ketone, aromatic and/or aliphatic hydrocarbons, vegetable or synthetic oils, DMF, liquid paraffin, light liquid paraffin, silicone, dimethylacetamide, N-methylpyrrolidone, and 2,2-dimethyl-4-oxy-methylene-1,3-dioxolane. Examples of the absorption accelerating substance include DMSO, isopropyl myristate, dipropylene glycol pelargonate, silicone oil, aliphatic esters, triglycerides, and aliphatic alcohols. Examples of the antioxidant include sulfites, metabisulfites, ascorbic acid, butylhydroxytoluene, butylated hydroxyanisole, and tocopherol.

The emulsifiable concentrate can be applied by an oral application, a percutaneous application, or an injection. The emulsifiable concentrate can be prepared by dissolving the I-form crystal, the II-form crystal, the III-form crystal, or the amorphous substance of the compound of Formula (1-1) in a hydrophobic phase or a hydrophilic phase and homogenizing the resultant solution with a solvent of another type of phase using an appropriate emulsifier, if necessary further together with an adjuvant such as a colorant, an absorption accelerating substance, a protective agent, an antioxidant, a sunscreen, and a thickener substance.

Examples of the hydrophobic phase (oil) include paraffin oil, silicone oil, sesame oil, almond oil, castor oil, synthetic triglyceride, ethyl stearate, di-n-butyryl adipate, hexyl laurate, dipropylene glycol pelargonate, an ester of a branched-chain aliphatic acid having a short chain length with a saturated aliphatic acid having a chain length of C16 to C18, isopropyl myristate, isopropyl palmitate, caprylate/caprate esters of a saturated aliphatic alcohol having a chain length of C12 to C18, isopropyl stearate, oleyl oleate, decyl oleate, ethyl oleate, ethyl lactate, a wax-like aliphatic acid ester, dibutyl phthalate, diisopropyl adipate, isotridecyl alcohol, 2-octyl dodecanol, cetylstearyl alcohol, and oleyl alcohol.

Examples of the hydrophilic phase include water, propylene glycol, glycerin, and sorbitol.

Examples of the emulsifier include: nonionic surfactants such as polyoxyethylated castor oil, polyoxyethylated monoolefin acid sorbitan, sorbitan monostearate, glycerin monostearate, polyoxyethyl stearate, and an alkylphenol polyglycol ether; amphoteric surfactants such as disodium N-lauryl β-iminodipropionate and lecithin; anionic surfactants such as sodium lauryl sulfate, an aliphatic alcohol sulfate other, and a mono-/di-alkyl polyglycol orthophosphate ester monoethanolamine salt; and cationic surfactants such as cetyltrimethylammonium chloride.

The composition containing the I-form crystal, the II-form crystal, the III-form crystal, or the amorphous substance of the compound of Formula (1-1) may further contain various adjuvants. Examples of the applicable adjuvant include a thickener, an organic solvent, an antifreezing agent, an antifoamer, an antifungal biocide, and a colorant, and each example of these examples is as follows.

The thickener is not particularly limited, and organic and inorganic natural products, synthetic products, and semi-synthetic products can be used. Examples thereof include: hetero polysaccharides such as xanthan gum, welan gum, and rhamsan gum; water-soluble polymer compounds such as polyvinyl alcohol, polyvinyl pyrrolidone, polyacrylic acid, sodium polyacrylate, and polyacrylamide; cellulose derivatives such as methylcellulose, carboxymethyl cellulose, carboxyethyl cellulose, hydroxyethyl cellulose, and hydroxypropyl cellulose; smectite-type clay minerals such as montmorillonite, saponite, hectorite, bentonite, Laponite, and synthetic smectite. These thickeners may be used individually or in combination of two or more types thereof, and the combination ratio may freely be selected. These thickeners may be added either as it is or as a dispersion in which the thickener is dispersed in water in advance. The content thereof in the composition of the present invention may also be freely selected.

Examples of the antifreezing agent include ethylene glycol, diethylene glycol, propylene glycol, and glycerin. Among them, preferred are propylene glycol and glycerin. The content thereof in the composition of the present invention may also be freely selected.

Examples of the other adjuvant include carboxymethyl cellulose, methyl cellulose, polyacrylate, alginate, gelatin, gum arabic, polyvinylpyrrolidone, polyvinyl alcohol, methyl vinyl ether, a copolymer of maleic anhydride, polyethylene glycol, wax, and colloidal silica.

The semisolid preparation can be applied by applying or spreading the preparation on the skin or by introducing the preparation into a body cavity. The gel can be prepared by adding to a solution prepared as described above with respect to the soluble concentrate for injection, a thickener in an amount sufficient for generating an ointment-like transparent substance having viscosity.

There may further be blended in an antifoamer such as a silicone-based emulsion, an antifungal biocide, and a colorant.

These preparations may also be prepared by mixing these preparations with other parasite control agents such as: organic phosphorus-based insecticides such as fenthion, trichlorfon, diazinon, dichlorvos, fenchlorphos, cythioate, propetamphos, malathion, fenitrothion, and cyanophos; carbamate-based insecticides such as propoxur and carbaryl; pyrethroid-based insecticide such as pyrethrin, permethrin, allethrin, resmethrin, flumethrin, phenothrin, and tetramethrin; IGR agents such as hexaflumuron, lufenuron, pyriproxyfen, and methoprene; neonicotinoid-based insecticides such as imidacloprid, nitenpyram, acetamiprid, thiamethoxam, thiacloprid, clothianidin, and dinotefuran; phenylpyrazole-based insecticides such as fipronil and ethiprole; macrolides such as ivermectin, eprinomectine, selamectin, milbemycin D, milbemycin oxime, and moxidectine; benzimidazoles such as flupentazole, parpentazole, triclapentazole, fenpentazole, and febantel; sulfa, drugs such as sulfadimethoxine and sulfamonomethoxine; piperazine; praziquantel; nitroscanate; pyrantel pamoate; bunamidine; dichlorophen; disophenol; arecoline; butyl chloride; metronidazole; acrinamine; melarsonyl; melarsomine; thiacetarsamide; dithiazanine; levamisole; and diethylcarbamazine.

Although the production method of a preparation containing the I-form crystal, the II-form crystal, the III-form crystal, or the amorphous substance of the compound of Formula (1-1) is not particularly limited, the preparation can be obtained by adding each of the above-described components to a dispersion medium and by mixing the resultant dispersion with a stirring machine. If necessary, the I-form crystal, the II-form crystal, the III-form crystal, or the amorphous substance of the compound of Formula (1-1), a surfactant, and other adjuvants may be individually or as a combination thereof fine-ground with a dry or wet grinder.

Dry grinding can be performed with a hammer mill, a pin mill, a jet mill, a ball mill, a roll mill, or the like. Fine-grinding by wet grinding can be performed with a wet grinder such as an inline mill and a beads mill.

The preparation containing the I-form crystal, the II-form crystal, the III-form crystal, or the amorphous substance of the compound of Formula (1-1) can be applied, for example, by a method of spraying a concentrate of the preparation or a diluted concentrate prepared, by diluting the concentrate with water to around 50 to 5,000 times to a crop, a tree, or a soil in which they grow using a sprayer or the like, or by a method of spraying a concentrate of the preparation or a diluted concentrate prepared by diluting the concentrate with water to around 2 to 100 times from the air using a helicopter or the like.

Next, examples of the formulation of the preparation in the case of using the I-form crystal, the II-form crystal, the III-form crystal, or the amorphous substance of the compound of Formula (1-1) are described, with the proviso that the formulation examples of the present invention are not limited to these examples. Here, in the following formulation examples, "part" means a part by weight.

(Wettable Powder)

| | |
|---|---|
| I-form crystal, II-form crystal, III-form crystal, or amorphous substance of compound of Formula (1-1) | 0.1 to 80 parts |
| Solid carrier | 5 to 98.9 parts |
| Surfactant | 1 to 10 part(s) |
| Others | 0 to 5 parts |

Examples of the others include an anticaking agent and a stabilizer.

(Emulsifiable Concentrate)

| | |
|---|---|
| I-form crystal, II-form crystal, III-form crystal, or amorphous substance of compound of Formula (1-1) | 0.1 to 30 parts |
| Liquid carrier | 45 to 95 parts |
| Surfactant | 4.9 to 15 parts |
| Others | 0 to 10 parts |

Examples of the others include a spreader and a stabilizer.

(Suspension Concentrate)

| | |
|---|---|
| I-form crystal, II-form crystal, III-form crystal, or amorphous substance of compound of Formula (1-1) | 0.1 to 70 parts |
| Liquid carrier | 15 to 98.89 parts |
| Surfactant | 1 to 12 part(s) |
| Others | 0.01 to 30 parts |

Examples of the others include an antifreezing agent and a thickener.

(Water Dispersible Granule)

| | |
|---|---|
| I-form crystal, II-form crystal, III-form crystal, or amorphous substance of compound of Formula (1-1) | 0.1 to 90 parts |
| Solid carrier | 0 to 98.9 parts |
| Surfactant | 1 to 20 part(s) |
| Others | 0 to 10 parts |

Examples of the others include a binder and a stabilizer.

(Soluble Concentrate)

| | |
|---|---|
| Compound of the present invention | 0.01 to 70 parts |
| Liquid carrier | 20 to 99.99 parts |
| Others | 0 to 10 parts |

Examples of the others include an antifreezing agent and a spreader.

(Granule)

| | |
|---|---|
| I-form crystal, II-form crystal, III-form crystal, or amorphous substance of compound of Formula (1-1) | 0.01 to 80 parts |
| Solid carrier | 10 to 99.99 parts |
| Others | 0 to 10 parts |

Examples of the others include a binder and a stabilizer.
(Dustable Powder)

| | |
|---|---|
| I-form crystal, II-form crystal, III-form crystal, or amorphous substance of compound of Formula (1-1) | 0.01 to 30 parts |
| Solid carrier | 65 to 99.99 parts |
| Others | 0 to 5 parts |

Examples of the others include an antidrift agent and a stabilizer.

Next, examples of the preparation containing the compound of the present invention as an active ingredient are more specifically described; however the examples should not be construed as limiting the scope of the present invention.

Here, in the following formulation examples, "parts" means parts by weight.

Formulation Example 1

Wettable Powder

| | |
|---|---|
| I-form crystal, II-form crystal, III-form crystal, or amorphous substance of compound of Formula (1-1) | 20 parts |
| Pyrophyllite | 74 parts |
| SORPOL 5039 (trade name; TOHO Chemical Industry Co., LTD.; mixture of nonionic surfactant and anionic surfactant) | 4 parts |
| CARPLEX #80D (trade name; Shionogi & Co., Ltd.; synthetic hydrous silicic acid) | 2 parts |

The above are homogeneously mixed and ground to prepare a wettable powder.

Formulation Example 2

Emulsifiable Concentrate

| | |
|---|---|
| I-form crystal, II-form crystal, III-form crystal, or amorphous substance of compound of Formula (1-1) | 5 parts |
| Xylene | 75 parts |
| N-methylpyrrolidone | 15 parts |
| SORPOL 2680 (trade name; TOHO Chemical Industry Co., LTD.; mixture of nonionic surfactant and anionic surfactant) | 5 parts |

The above are homogeneously mixed to prepare an emulsifiable concentrate.

Formulation Example 3

Suspension Concentrate

| | |
|---|---|
| I-form crystal, II-form crystal, III-form crystal, or amorphous substance of compound of Formula (1-1) | 25 parts |
| AGRISOL S-710 (trade name; Kao Corporation; nonionic surfactant) | 10 parts |
| LUNOX 1000C (trade name; TOHO Chemical Industry Co., LTD.; anionic surfactant) | 0.5 parts |
| Xanthan gum | 0.2 parts |
| Water | 64.3 parts |

The above are homogeneously mixed and then wet-ground to prepare a suspension concentrate.

Formulation Example 4

Water Dispersible Granule

| | |
|---|---|
| I-form crystal, II-form crystal, III-form crystal, or amorphous substance of compound of Formula (1-1) | 75 parts |
| HITENOL NE-15 (trade name; Dai-ichi Kogyo Seiyaku Co., Ltd.; anionic surfactant) | 5 parts |
| VANILLEX N (trade name; Nippon Paper Industries Co., Ltd.; anionic surfactant) | 10 parts |
| CARPLEX #80D (trade name; Shionogi & Co., Ltd.; synthetic hydrous silicic acid) | 10 parts |

The above are homogeneously mixed and ground, and then stirred and mixed with a small amount of water, followed by being granulated with an extrusion granulator and dried to prepare a water dispersible granule.

Formulation Example 5

Granule

| | |
|---|---|
| I-form crystal, II-form crystal, III-form crystal, or amorphous substance of compound of Formula (1-1) | 5 parts |
| Bentonite | 50 parts |
| Talc | 45 parts |

The above are homogeneously mixed and ground, and then stirred and mixed with a small amount of water, followed by being granulated with an extrusion granulator and dried to prepare a granule.

Formulation Example 6

Dustable Powder

| | |
|---|---|
| I-form crystal, II-form crystal, III-form crystal, or amorphous substance of compound of Formula (1-1) | 3 parts |
| CARPLEX #80D (trade name; Shionogi & Co., Ltd.; synthetic hydrous silicic acid) | 0.5 parts |
| Kaolinite | 95 parts |
| Diisopropyl phosphate | 1.5 parts |

The above are homogeneously mixed and ground to prepare et dustable powder.

For using the preparation, the preparation is diluted with water by 1 to 10,000 time(s) to be sprayed or is directly sprayed without dilution.

Formulation Example 7

Wettable Powder Preparation

| | |
|---|---|
| I-form crystal, II-form crystal, III-form crystal, or amorphous substance of compound of Formula (1-1) | 25 parts |
| Sodium diisobutylnaphthalenesulfonate | 1 part |
| Calcium n-dodecylbenzenesulfonate | 10 parts |
| Alkylaryl polyglycol ether | 12 parts |
| Sodium salt of naphthalenesulfonic acid formalin condensate | 3 parts |
| Emulsion-type silicone | 1 part |
| Silicon dioxide | 3 parts |
| Kaolin | 45 parts |

Formulation Example 8

Water Soluble Thickener Preparation

| | |
|---|---|
| I-form crystal, II-form crystal, III-form crystal, or amorphous substance of compound of Formula (1-1) | 20 parts |
| Polyoxyethylene lauryl ether | 3 parts |
| Sodium dioctylsulfosuccinate | 3.5 parts |
| Dimethylsulfoxide | 37 parts |
| 2-propanol | 36.5 parts |

Formulation Example 9

Soluble Concentrate for Spraying

| | |
|---|---|
| I-form crystal, II-form crystal, III-form crystal, or amorphous substance of compound of Formula (1-1) | 2 parts |
| Dimethylsulfoxide | 10 parts |
| 2-propanol | 35 parts |
| Acetone | 53 parts |

Formulation Example 10

Soluble Concentrate for Percutaneous Application

| | |
|---|---|
| I-form crystal, II-form crystal, III-form crystal, or amorphous substance of compound of Formula (1-1) | 5 parts |
| Hexylene glycol | 50 parts |
| Isopropanol | 45 parts |

Formulation Example 11

Soluble Concentrate for Percutaneous Application

| | |
|---|---|
| I-form crystal, II-form crystal, III-form crystal, or amorphous substance of compound of Formula (1-1) | 5 parts |
| Propylene glycol monomomethyl ether | 50 parts |
| Dipropylene glycol | 45 parts |

Formulation Example 12

Soluble Concentrate for Percutaneous Application (Dropping)

| | |
|---|---|
| I-form crystal, II-form crystal, III-form crystal, or amorphous substance of compound of Formula (1-1) | 2 parts |
| Light liquid paraffin | 98 parts |

Formulation Example 13

Soluble Concentrate for Percutaneous Application (Dropping)

| | |
|---|---|
| I-form crystal, II-form crystal, III-form crystal, or amorphous substance of compound of Formula (1-1) | 2 parts |
| Light liquid paraffin | 58 parts |
| Olive oil | 30 parts |
| ODO-H | 9 parts |
| Shin-Etsu silicone | 1 part |

The raw material compound of Formula (3) used in the present invention can be synthesized according to, for example, a method described in WO 05/085216 Pamphlet in a manner of Reaction Formula 1:

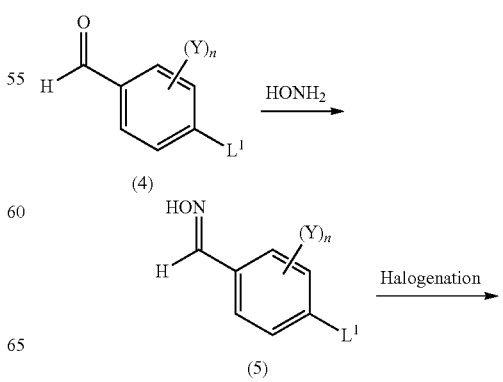

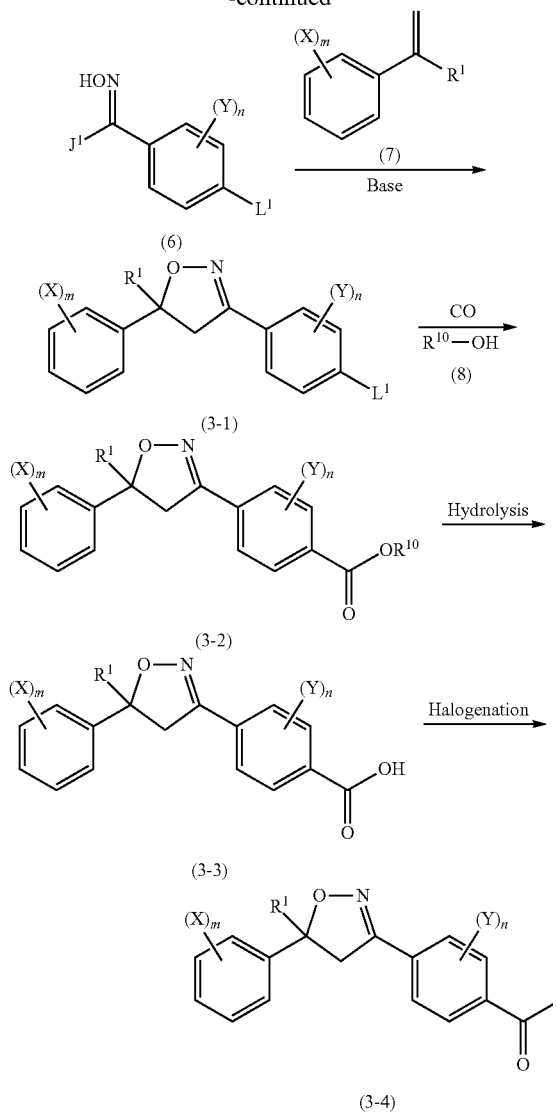

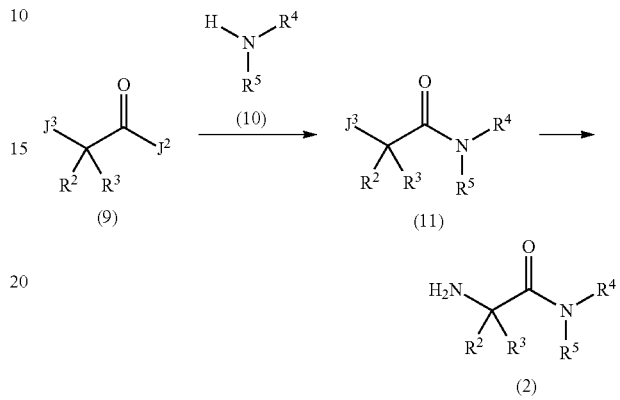

the same as defined above] can be obtained. Further, by halogenating a compound of General Formula (3-3), a compound of General Formula (3-4) [where X, Y, $R^1$, J, m, and n are the same as defined above] can be obtained.

The raw material compound of Formula (2) can be synthesized according to a publicly known method, for example in a manner of Reaction Scheme 2:

That is, by reacting a compound of General Formula (9) [where $R^2$ and $R^3$ are the same as defined above; $J^2$ is a halogen atom such as a chlorine atom and a bromine atom; and $J^3$ is a halogen atom such as a chlorine atom and a bromine atom, or phthalimide] with a compound of General Formula (10) [where $R^4$ and $R^5$ are the same as defined above] or a salt thereof, a compound of General Formula (11) [where $R^2$, $R^3$, $R^4$, $R^5$, and $J^3$ are the same as defined above] is produced, and by subjecting the compound of General Formula (11), when $J^3$ is a halogen atom, to amination, and when $J^3$ is phthalimide, to phthaloyl-elimination, a compound of General Formula (2) [where $R^2$, $R^3$, $R^4$, and $R^5$ are the same as defined above] can be obtained.

EXAMPLES

Hereinafter, there are described Examples of the present invention which should not be construed as limiting the scope of the present invention.

That is, by reacting a compound of General Formula (4) [where Y and n are the same as defined above; $L^1$ is a chlorine atom, a bromine atom, an iodine atom, or —$OSO_2R^9$; and $R^9$ is the same as defined above] with hydroxylamine or a salt thereof, a compound of General Formula (5) [where Y, $L^1$, and n are the same as defined above] is produced. Then, by converting the compound of General Formula (5) with a halogenating agent to a compound of General Formula (6) [where Y, $L^1$, and n are the same as defined above; and $J^1$ is a halogen atom such as a chlorine atom and a bromine atom] and further by reacting the compound of General Formula (6) with a compound of General Formula (7) [where X, $R^1$, and m are the same as defined above] in the presence ea base, a compound of General Formula (3-1) [where X, Y, $R^1$, $L^1$, m, and n are the same as defined above] can be obtained. By reacting a compound of General Formula (3-1) with carbon monoxide in the co-presence of a compound of General Formula (8) [where $R^{10}$ is the same as defined above], a compound of General Formula (3-2) [where X, Y, $R^1$, $R^{10}$, m, and n are the same as defined above] can be obtained, and by hydrolyzing a compound of General Formula (3-2), a compound of General Formula (3-3) [where X, Y, $R^1$, m, and n are Example 1

Production of 4-[5-(3,5-dichlorophenyl)-5-trifluoromethyl-4,5-dihydroisoxazole-3-yl]-2-methyl-N-N-(2,2,2-trifluoroethyl)carbamoylmethyl]benzoic acid amide Reaction Condition 1-1

Into a 100 mL pressurized reaction vessel, 3.00 g (6.62 mmol) of 3-(4-bromo-3-methylphenyl)-5-(3,5-dichlorophenyl)-5-trifluoromethyl-4,5-dihydroisoxazole (2-1), 1.24 g (7.95 mmol) of 2-amino-N-(2,2,2-trifluoroethyl)acetic acid amide, 1.1 g (7.95 mmol) of potassium carbonate, 41.0 mg (0.099 mmol) of 1,3-bis(diphenylphosphino)propane, 0.14 g (0.033 mmol) of 5% palladium-carbon (50% water content-product), and 30 mL of 1,2-dimethoxyethane were charged, and the inside of the reaction vessel was purged with nitrogen and carbon monoxide in this order at room temperature, followed by filling the reaction vessel with carbon monoxide to 1.0 MPa. Then, the reaction vessel was heated to 105° C., and at the same temperature, the reaction was carried out while stirring the reaction mixture for 5 hours. During the reaction, the inside pressure was elevated to maximum of 1.3 MPa.

Then, the reaction vessel was cooled down to room temperature, and the pressure inside the reaction vessel was returned to atmospheric pressure, followed by purging the inside of the reaction vessel with nitrogen. Insoluble matters in the reaction solution were filtered off by Celite filtration, and the Celite was washed with ethyl acetate and water. To the resultant filtrate, concentrated hydrochloric acid was added to make the filtrate acidic, and the aqueous phase was separated off, followed by washing the organic phase with a sodium chloride aqueous solution. The organic phase was dried over anhydrous magnesium sulfate, followed by filtering off, and from the resultant organic phase, a solvent was distilled off under reduced pressure. The resultant residue was subjected to crystallization using 3/18 (mL) of ethyl acetate/hexane to obtain 2.54 g (437 mmol) of the aimed product as a pale yellow solid.

Reaction Condition 1-2

A solution of 0.25 g (0.59 mmol) of 4-[5-(3,5-dichlorophenyl)-5-trifluoromethyl-4,5-dihydroisoxazole-3-yl]-2-methylbenzoic acid in 3 mL of N,N-dimethylformamide was ice-cooled, and thereto, 0.10 mL (0.72 mmol) of triethylamine and 0.20 g (0.72 mmol) of diphenylphosphoryl azide were added, followed by stirring the resultant reaction mixture under ice cooling for 1 hour. Thereto, further 0.10 g (0.66 mmol) of 2-amino-N-(2,2,2-trifluoroethyl)acetic acid amide was added, and the resultant reaction mixture was stirred at room temperature over one night. The reaction solution was analyzed by high-performance liquid chromatography, and the relative area of the aimed product at 254 nm was found to be 94.12%.

Reaction Condition 1-3

To a solution of 0.84 g (2.00 mmol) of 4-[5-(3,5-dichlorophenyl)-5-trifluoromethyl-4,5-dihydroisoxazole-3-yl]-2-methylbenzoic acid in 2 mL of acetonitrile, 0.57 g (4.00 mmol) of dimethylsulfamoyl chloride was added while stirring the solution, and the resultant reaction mixture was warmed to 40° C. Into the reaction mixture, a solution of 0.34 g (2.20 mmol) of 2-amigo-N-(2,2,2-trifluoroethyl)acetic acid amide, 0.61 g (6.00 ramp of n-butyldimethylamine, and 24 mg (0.20 mmol) of 4-dimethylaminopyridine in 2 mL of acetonitrile was dropped, and the resultant reaction mixture was stirred at 40° C. for 2 hours. Then, the reaction solution was left to be cooled down, and thereto, ice water was added, followed by extracting the reaction mixture with ethyl acetate three times. The organic phases were combined, and the resultant organic phase was washed with brine, followed by drying the organic phase over anhydrous sodium sulfate. From the organic phase, a solvent was distilled off under reduced pressure, and the resultant residue was purified by silica gel column chromatography eluting with ethyl acetate-hexane (1:3) to obtain 0.92 g (1.65 mmol) of the aimed product.

Reaction Condition 1-4

In a nitrogen atmosphere, a solution of 1.50 g (9.6 mmol) of 2-amino-N-(2,2,2-trifluoroethyl)acetic acid amide in 20 g of ethyl acetate was cooled down to 5° C., and thereto, 1.11 g (11.0 mmol) of triethylamine was added. Into the resultant reaction mixture, a solution of 4.0 g (9.2 mmol) of 4-[5-(3,5-dichlorophenyl)-5-trifluoromethyl-4,5-dihydroisoxazole-3-yl]-2-methylbenzoic acid chloride in 32 g of toluene was dropped at a dropping speed by which the temperature of the reaction solution did not exceed 10° C., and the resultant reaction mixture was stirred at 20° C. for 1 hour. After the completion of the reaction, to the reaction mixture, 28 g of water and 28 g of ethyl acetate were added, and an organic phase obtained after the phase separation was washed with a diluted hydrochloric acid (prepared by diluting 2.0 g of concentrated hydrochloric acid with 18.3 g of water) and next with 20 g of brine. To the resultant organic phase, 1.2 g of an activated carbon was added, and the resultant mixture was stirred at 40° C. for 1 hour, followed by cooling down the organic phase to 20° C. and by removing the activated carbon from the organic phase by Celite filtration. By distilling off a solvent under reduced pressure to concentrate the organic phase, 19.5 g of a solution containing the aimed product was obtained. To the resultant solution, 12 g of ethyl acetate was added, and further, 28 g of hexane was added to cool down the resultant reaction mixture to 5° C. A precipitated crystal was retrieved by reduced pressure-filtration and was dried under reduced pressure to obtain 5.0 g (9.0 mmol) of the aimed product as a white solid.

Reaction Condition 1-5

In a nitrogen atmosphere, an aqueous solution in which 0.46 g (11.45 mmol) of sodium hydroxide was dissolved in 25 g of water and 7.1 g (11.96 mmol) of a 26.3 wt. % 2-amino-N-(2,2,2-trifluoroethyl)acetic acid amide aqueous solution were charged into a 200 mL four-neck flask, and the resultant reaction mixture was heated to 40° C. Into the reaction mixture, a solution of 5.0 g (11.45 mmol) of 4-[5-(3,5-dichlorophenyl)-5-trifluoromethyl-4,5-dihydroisoxazole-3-yl]-2-methylbenzoic acid chloride in 35 g of toluene heated to 40° C. was gradually dropped, and at the same temperature the reaction was stirred for 1 hour. The resultant slurry was cooled down to 0° C. and was stirred for 30 minutes while maintaining the temperature. The precipitated solid was filtered, and the solid on a funnel was washed with 50 g of water two times and then with 50 g of toluene cooled down to 5° C. one time, followed by drying the solid under reduced pressure to obtain 5.9 g (10.6 mmol) of the aimed product as a white solid.

Example 2

From a solution of 25.0 g of the compound (1-1) in a solvent mixture of 118 mL of ethyl acetate and 56 mL of toluene, insoluble matters were removed by reduced pressure-filtration, and the solvent was distilled off under reduced pressure. To the solution in a state in which the solvent remained in an amount of 1 part by weight based on the amount of the compound (1-1), 25 g of ethyl acetate and 124 g of toluene were added, and the resultant reaction mixture was heated to 90° C. while stirring the reaction mixture. While the vacuum degree is adjusted so that the solvent refluxes, the reaction mixture was gradually cooled down to 60° C., and the precipitation of a solid was confirmed at around 70° C. Then, the reaction mixture was cooled down to 0° C. under, atmospheric pressure and was stirred at 0 to 5° C. for 1 hour, and a solid was retrieved by reduced pressure-filtration (washed with 50 g of toluene), followed by drying the solid to obtain 22.8 g of a solid. The obtained solid was found to be a I-form crystal of which powder X-ray diffraction pattern exhibits substantially the same as that of FIG. 1 (the diffraction angle (2θ) of the powder X-ray diffraction spectrum has peaks at 4.4°, 8.7°, 11.1°, 13.1°, 14.4°, 14.8°, 16.3°, 16.9°, 17.4°, 17.7°, 18.1°, 18.8°, 19.4°, 21.2°, 21.9°, 22.3°, 23.0°, 2.39°, 24.5°, 25.0°, 26.3°, and 27.3°).

Example 3

Into a 50 μL flask, 0.5 g of the compound (1-1) was charged, and thereto, a solution mixture of 5 mL of tetrahydrofuran (THF) and 5 mL of water were charged, followed by stirring the resultant reaction mixture to obtain an emulsion solution. The solution was filtered under reduced pressure and was transferred into a conical flask. The conical flask was hermetically sealed and was left stationary for 50 days. There was not observed the precipitation of a solid in the flask, so that the flask was brought into an unsealed state by displacing a ping, and the flask in such a state was left stationary for further 7 days. Then, there was confirmed the precipitation of a solid in the flask. The flask was left stationary for further 19 days. The precipitated solid was crushed with a spatula, was retrieved by filtration under reduced pressure (washed with water), and was dried to obtain 0.41 g of a solid. The obtained solid was found to be a II-form crystal of which powder X-ray diffraction pattern exhibits substantially the same as that of FIG. 2 (the diffraction angle (2θ) of the powder X-ray diffraction spectrum has peaks at 10.2°, 12.3°, 14.7°, 15.9°, 18.4°, 20.1°, 21.2°, 22.0°, 22.8°, 24.6°, and 26.6°).

Example 4

3.69 g of the compound (1-1) was dissolved in 8 mL of tetrahydrofuran (THF), and the resultant solution was filtered (washing a THF-soluble matter in a filtered matter with 2 mL of THF into the solution). On the other hand, into a 100 mL conical flask, 20 mL of water was charged, and thereto, a THF solution containing the filtered compound (1-1) (with a wash liquid of 2 mL of THF) was charged, followed by strongly shaking the flask. Thereto, 30 mg of the II-form crystal of the compound (1-1) was added as a seed crystal, and the flask in an unsealed state was left stationary for 6 days. A precipitated solid was crushed with a spatula, was retrieved by filtration under reduced pressure (washed with water), and was dried to obtain 3.5 g of a solid. The obtained solid was found to be a II-form crystal of which powder X-ray diffraction pattern exhibits substantially the same as that of FIG. 2 in which the diffraction angle (2θ) of the powder X-ray diffraction spectrum has peaks at 10.2°, 12.3°, 14.7°, 15.9°, 18.4°, 20.1°, 21.2°, 22.0°, 22.8°, 24.6°, and 26.6°.

Example 5

10 g of the compound (1-1) was dissolved in 50 mL of ethyl acetate, and the resultant solution was filtered (washing an ethyl acetate-soluble matter in a filtered matter with 30 ml, of ethyl acetate into the solution). On the other hand, into a 1,000 mL, four-neck flask, 400 mL of n-hexane was charged, and the flask was cooled down to 5° C. or less in a nitrogen atmosphere. Thereinto, an ethyl acetate solution containing the filtered compound (1-1) was dropped over 30 minutes, and the resultant reaction mixture was stirred at 5° C. or less for 30 minutes. A precipitated solid was retrieved by filtration under reduced pressure (washed with 40 mL, of n-hexane) and was dried to obtain 9.3 g of a solid. The obtained solid was found to be a III-form crystal of which powder X-ray diffraction pattern exhibits substantially the same as that of FIG. 3 in which the diffraction angle (2θ) of the powder X-ray diffraction spectrum has peaks at 4.3°, 8.7°, 11.1°, 14.4°, 16.3°, 16.9°, 17.4°, 17.7°, 18.7°, 19.4°, 19.9°, 21.2°, 21.8°, 22.3°, 23.8°, 24.4°, 24.9°, and 26.2°.

Example 6

15 g of the compound (1-1) was dissolved in 15 g of dimethylsulfoxide (DMSO) while warming dimethylsulfoxide at 40 to 50° C., and the resultant solution was filtered (washing a DMSO-soluble matter in a filtered matter with 5 g of DMSO into the solution). On the other hand, into a 300 mL four-neck flask, 150 g of water was charged, and the flask was cooled down to 5° C. or less. Thereinto, a DMSO solution containing the filtered compound (1-1) (with a wash liquid of 5 g of DMSO) was dropped over 25 minutes, and the resultant reaction mixture was stirred at 5° C. or less for 1 hour. A hydrous product of the obtained compound (1-1) was washed again with 150 g of water, and a solid was filtered under reduced pressure to obtain 40.3 g of a hydrous solid. The powder X-ray diffraction spectrum of the obtained hydrous solid is shown in FIG. 4. The obtained hydrous solid was an amorphous substance having no diffraction peak.

Here, by drying 3.05 g of the obtained hydrous solid under reduced pressure, 1.01 of a solid was obtained, so that the content of the amorphous substance in the hydrous solid was found to be 33% by weight (water content: 67% by weight), and the dried solid was found to be a I-form crystal of which powder X-ray diffraction pattern exhibits substantially the same as that of FIG. 1.

Example 7

0.4 g of a III-form crystal of the compound (1-1) obtained in the same manner as in Example 5 was suspended in 5 mL of toluene at room temperature, and the resultant suspension was stirred for 7 days. Then, a solid was retrieved by filtration under reduced pressure, and a solvent was naturally dried to obtain 0.34 g of the solid. The obtained solid was found to be a I-form crystal of which powder X-ray diffraction pattern exhibits substantially the same as that of FIG. 1.

Example 8

0.4 g of a III-form crystal of the compound (1-1) obtained in the same manner as in Example 5 was suspended in 2 mL of methanol at room temperature, and the resultant suspension was stirred for 7 days. Then, a solid was retrieved by filtration under reduced pressure, and a solvent was naturally dried to obtain 0.31 g of the solid. The obtained solid was found to be a II-form crystal of which powder X-ray diffraction pattern exhibits substantially the same as that of FIG. 2.

Example 9

1.2 g of a hydrous amorphous substance of the compound (1-1) immediately after obtained by the operation of Example 6 was suspended in 5 mL of toluene at room temperature, and the resultant suspension was stirred for 7 days. Then, a solid was retrieved by filtration under reduced pressure, and a solvent was naturally dried to obtain, 0.34 g of the solid. The obtained solid was found to be a I-form crystal of which powder X-ray diffraction pattern exhibits substantially the same as that of FIG. 1.

INDUSTRIAL APPLICABILITY

The production method according to the present invention is an industrial production method of an isoxazoline-substituted benzoic acid amide compound having excellent pest control effect.

The invention claimed is:
1. A process of preparing an isoxazoline-substituted benzoic acid amide compound of Formula (1):

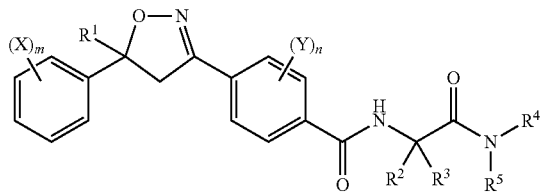

(1)

[where X is a halogen atom, cyano, nitro, —SF$_5$, C$_{1-6}$ alkyl, C$_{1-6}$ haloalkyl, hydroxy(C$_{1-6}$)alkyl, hydroxy(C$_{1-6}$)haloalkyl, C$_{1-6}$ alkoxy(C$_{1-6}$)alkyl, C$_{1-6}$ haloalkoxy (C$_{1-6}$) alkyl, C$_{1-6}$ alkoxy(C$_{1-6}$)haloalkyl, C$_{1-6}$ haloalkoxy (C$_{1-6}$) haloalkyl, C$_{3-8}$ cycloalkyl, C$_{3-8}$ halocycloalkyl, —OR$^6$, —OSO$_2$R$^6$, —S(O),R$^6$, or —N(R$^8$)R$^7$, where when m is 2 or more, Xs are optionally the same as or different from each other, Y is a halogen atom, cyano, nitro, C$_{1-6}$ alkyl, C$_{1-6}$ haloalkyl, C$_{1-6}$ alkoxy, C$_{1-6}$ haloalkoxy, C$_{1-6}$ alkylthio, C$_{1-6}$ haloalkylthio, C$_{1-6}$ alkylsulfonyl, C$_{1-6}$ haloalkylsulfonyl, or —N(R$^8$)R$^7$, where when n is 2 or more, Ys are optionally the same as or different from each other, R$^1$ is a hydrogen atom, C$_{1-6}$ alkyl, C$_{1-6}$ haloalkyl, C$_{3-8}$ cycloalkyl, or C$_{3-8}$ halocycloalkyl, R$^2$ is a hydrogen atom, cyano, C$_{1-6}$ alkyl, or C$_{1-6}$ haloalkyl, R$^3$ is a hydrogen atom or C$_{1-6}$ alkyl, or R$^3$ together with R$^2$ optionally form a C$_{2-5}$ alkylene chain to form together with a carbon atom to which R$^3$ is bonded a 3- to 6-membered ring, and at this time, the alkylene chain optionally contains one oxygen atom, one sulfur atom, or one nitrogen atom, R$^4$ is a hydrogen atom, C$_{1-6}$ alkyl, C$_{1-6}$ alkyl optionally substituted with R$^{11}$, C$_{1-6}$ haloalkyl, C$_{3-8}$ cycloalkyl, C$_{3-8}$ halocycloalkyl, C$_{3-6}$ alkenyl, C$_{3-6}$ haloalkenyl, C$_{3-6}$ alkynyl, phenyl, or phenyl substituted with (Z)$_r$, R$^5$ is a hydrogen atom, C$_{1-6}$ alkyl, C$_{1-6}$ haloalkyl, C$_{3-8}$ cycloalkyl, C$_{3-8}$ halocycloalkyl, —CHO, C$_{1-6}$ alkylcarbonyl, C$_{1-6}$ haloalkylcarbonyl, C$_{1-6}$ alkoxycarbonyl, C$_{1-6}$ alkylsulfonyl, or C$_{1-6}$ haloalkylsulfonyl, or R$^5$ together with R$^4$ optionally form a C$_{2-6}$ alkylene chain to form together with a nitrogen atom to which R$^5$ is bonded a 3- to 7-membered ring, and at this time, the alkylene chain optionally contains one oxygen atom, one sulfur atom, or one nitrogen atom and is optionally substituted with a halogen atom, a C$_{1-6}$ alkyl group, a C$_{1-6}$ alkoxy group, a formyl group, a C$_{1-6}$ alkylcarbonyl group, a C$_{1-6}$ alkoxycarbonyl group, an oxo group, or a thioxo group, R$^6$ is C$_{1-6}$ alkyl, C$_{1-4}$ alkoxy(C$_{1-4}$)alkyl, C$_{1-6}$ haloalkyl, or C$_{1-4}$ haloalkoxy(C$_{1-4}$) haloalkyl, R$^7$ is C$_{1-6}$ alkyl, —CHO, C$_{1-6}$ alkylcarbonyl, C$_{1-6}$ haloalkylcarbonyl, C$_{1-6}$ alkoxycarbonyl, C$_{1-6}$ alkylsulfonyl, or C$_{1-6}$ haloalkylsulfonyl, R$^8$ is a hydrogen atom or C$_{1-6}$ alkyl, R$^{11}$ is cyano, C$_{3-8}$ cycloalkyl, C$_{3-8}$ halocycloalkyl, —OR$^6$, —S(O),R$^6$, —N(R$^8$)R$^7$, phenyl, or phenyl substituted with (Z)$_1$, Z is a halogen atom, cyano, nitro, C$_{1-6}$ alkyl, C$_{1-6}$ haloalkyl, C$_{3-8}$ cycloalkyl, C$_{3-8}$ halocycloalkyl, —OR$^6$, —OSO$_2$R$^6$, —S(O),R$^6$, or —N(R$^8$)R$^7$, where when t is 2 or more, Zs are optionally the same as or different from each other, m is an integer of 0 to 5, n is an integer of 0 to 4, r is an integer of 0 to 2, and t is an integer of 1 to 5], the production method comprising: reacting an isoxazoline-substituted benzene compound of Formula (3):

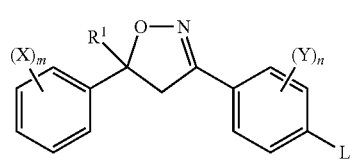

(3)

[where X, Y, R$^1$, m, and n are the same as defined above,

L is a chlorine atom, a bromine atom, an iodine atom, —OSO$^2$R$^9$, —C(O)OH, —C(O)OR$^{10}$, or —C(O)J, R$^9$ is C$_{1-6}$ alkyl, C$_{1-6}$ haloalkyl, phenyl, or phenyl substituted with (Z)$_r$, R$^{10}$ is C$_{1-6}$ alkyl, C$_{1-4}$ alkoxy(C$_{1-4}$)alkyl, C$_{1-6}$ haloalkyl, C$_{1-4}$ haloalkoxy(C$_{1-4}$) haloalkyl, benzyl, phenyl, or phenyl substituted with (Z)$_r$, Z, r and t are the same as defined above, and J is a halogen atom], with a 2-aminoacetic acid amide compound of Formula (2):

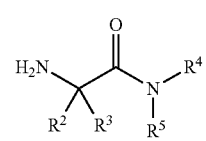

(2)

[where R$^2$, R$^3$, R$^4$, and R$^5$ are the same as defined above] or a salt thereof.

2. The process of preparing an isoxazoline-substituted benzoic acid amide compound according to claim 1, wherein a compound of Formula (3) (where L is a chlorine atom, a bromine atom, an iodine atom, or —OSO$_2$R$^9$) is reacted with a compound of Formula (2) in the presence of carbon monoxide and a palladium catalyst.

3. The process of preparing an isoxazoline-substituted benzoic acid amide compound according to claim 1, wherein a compound of Formula (3) (where L is —C(O)OH) is reacted with a compound of Formula (2) in the presence of a condensing agent.

4. The process of preparing an isoxazoline-substituted benzoic acid amide compound according to claim 1, wherein a compound of Formula (3) (where L is —C(O)OR$^{10}$ or —C(O)J) is reacted with a compound of Formula (2) in the presence of a base.

5. The process of preparing a compound of Formula (1-1):
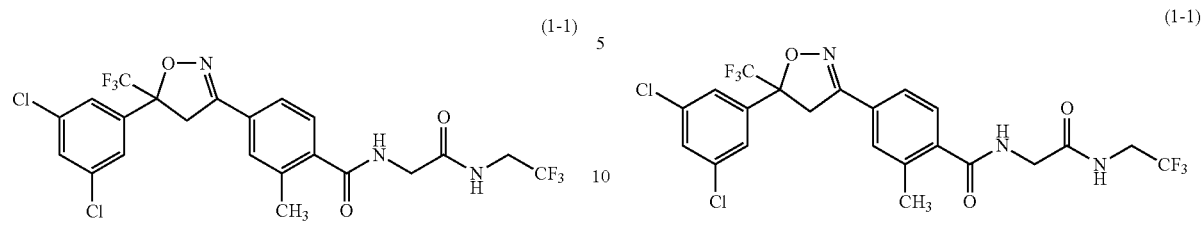
(1-1)
according to claim 1.
6. The process of preparing a compound of Formula (1-1):
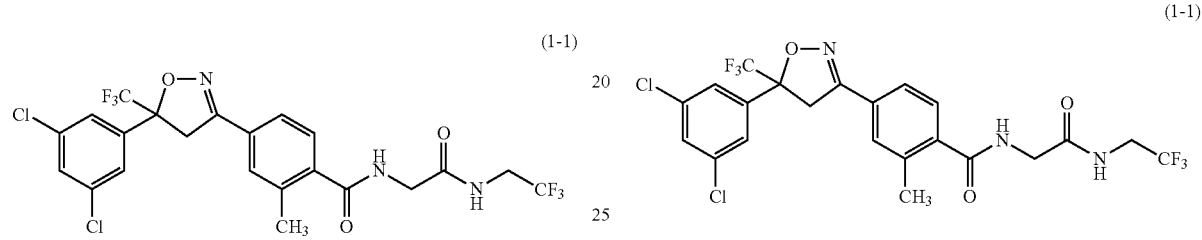
(1-1)
according to claim 2.
7. The process of preparing a compound of Formula (1-1):
(1-1)
according to claim 3.
8. The process of preparing a compound of Formula (1-1):
(1-1)
according to claim 4.
* * * * *